United States Patent
Ugalde et al.

(10) Patent No.: US 12,146,180 B2
(45) Date of Patent: *Nov. 19, 2024

(54) METHODS FOR PRODUCING BIOMASS RICH IN DHA, PALMITIC ACID AND PROTEIN USING A EUKARYOTIC MICROORGANISM

(71) Applicant: MARA RENEWABLES CORPORATION, Dartmouth (CA)

(72) Inventors: Violeta Ugalde, Dartmouth (CA); Zachary Sun, Dartmouth (CA); Anthony Windust, Dartmouth (CA); Roberto E. Armenta, Dartmouth (CA)

(73) Assignee: MARA RENEWABLES CORPORATION, Dartmouth (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/533,771

(22) Filed: Nov. 23, 2021

(65) Prior Publication Data

US 2022/0177934 A1 Jun. 9, 2022

Related U.S. Application Data

(62) Division of application No. 15/845,697, filed on Dec. 18, 2017, now Pat. No. 11,198,891.

(60) Provisional application No. 62/437,886, filed on Dec. 22, 2016.

(51) Int. Cl.

| | |
|---|---|
| C12P 7/6434 | (2022.01) |
| A23K 10/18 | (2016.01) |
| A23K 20/147 | (2016.01) |
| A23K 20/158 | (2016.01) |
| A23K 50/00 | (2016.01) |
| A23L 33/115 | (2016.01) |
| A23L 33/135 | (2016.01) |
| C12N 1/10 | (2006.01) |
| C12N 1/12 | (2006.01) |
| C12N 1/14 | (2006.01) |
| C12P 7/6409 | (2022.01) |
| C12P 7/6427 | (2022.01) |
| C12P 7/6472 | (2022.01) |
| C12P 21/00 | (2006.01) |
| C12P 23/00 | (2006.01) |
| C12R 1/645 | (2006.01) |
| C12R 1/89 | (2006.01) |

(52) U.S. Cl.
CPC ............ *C12P 7/6434* (2022.01); *A23K 10/18* (2016.05); *A23K 20/147* (2016.05); *A23K 20/158* (2016.05); *A23K 50/00* (2016.05); *A23L 33/115* (2016.08); *A23L 33/135* (2016.08); *C12N 1/10* (2013.01); *C12N 1/12* (2013.01); *C12N 1/125* (2021.05); *C12N 1/14* (2013.01); *C12N 1/145* (2021.05); *C12P 7/6409* (2013.01); *C12P 7/6427* (2013.01); *C12P 7/6472* (2013.01); *C12P 21/00* (2013.01); *C12P 23/00* (2013.01); *A23V 2002/00* (2013.01); *C12R 2001/645* (2021.05); *C12R 2001/89* (2021.05)

(58) Field of Classification Search
CPC ....... C12P 23/00; C12P 7/6409; C12P 7/6472; C12P 21/00; A23K 20/147; A23K 20/158; A23K 50/00; A23K 10/18; A23L 33/115; A23L 33/135; C12N 1/125; C12N 1/145; C12N 1/10; C12N 1/12; C12N 1/14; C12R 2001/645; C12R 2001/89; A23V 2002/00
USPC ......................................................... 435/67
See application file for complete search history.

(56) References Cited

U.S. PATENT DOCUMENTS

| | | |
|---|---|---|
| 500,513 A | 6/1893 | Sample |
| 5,374,657 A | 12/1994 | Kyle |
| 5,397,591 A | 3/1995 | Kyle et al. |
| 6,582,941 B1 | 6/2003 | Yokochi et al. |
| 8,617,857 B2 | 12/2013 | Seo et al. |
| 9,023,616 B2 | 5/2015 | Radianingtyas et al. |
| 9,476,074 B2 | 10/2016 | Pora et al. |
| 2001/0025114 A1 | 9/2001 | Bijl et al. |
| 2003/0143659 A1 | 7/2003 | Bijl et al. |
| 2003/0161864 A1 | 8/2003 | Tanaka et al. |
| 2004/0092590 A1 | 5/2004 | Arterburn et al. |
| 2004/0161831 A1 | 8/2004 | Komazawa et al. |
| 2005/0027004 A1 | 2/2005 | Kyle et al. |
| 2005/0129831 A1 | 6/2005 | Fabritius |
| 2005/0170479 A1 | 8/2005 | Weaver et al. |
| 2007/0003686 A1 | 1/2007 | Fichtali et al. |
| 2007/0104856 A1 | 5/2007 | Standal et al. |
| 2007/0112071 A1 | 5/2007 | Bryhn et al. |
| 2007/0184090 A1 | 8/2007 | Van Waterschoot et al. |

(Continued)

FOREIGN PATENT DOCUMENTS

| | | |
|---|---|---|
| CN | 101252844 A | 8/2008 |
| EP | 0707487 A1 | 4/1996 |

(Continued)

OTHER PUBLICATIONS

Sequence alignment of SEQ ID No. 1 of Seo et al. with instant SEQ ID No. 1, Result 5, Performed May 13, 2023.*

(Continued)

*Primary Examiner* — Jennifer M. H. Tichy
(74) *Attorney, Agent, or Firm* — Kilpatrick Townsend & Stockton LLP

(57) ABSTRACT

Provided herein are eukaryotic microorganisms having a simple lipid profile comprising long chain fatty acids (LCFAs). Also provided are compositions and cultures comprising the eukaryotic microorganisms as well as methods of using the eukaryotic microorganisms.

20 Claims, 6 Drawing Sheets
Specification includes a Sequence Listing.

(56) References Cited

U.S. PATENT DOCUMENTS

| | | |
|---|---|---|
| 2007/0243307 A1 | 10/2007 | Abril et al. |
| 2007/0248586 A1 | 10/2007 | Arterburn et al. |
| 2009/0064567 A1 | 3/2009 | Lippmeier et al. |
| 2009/0209014 A1 | 8/2009 | Chi et al. |
| 2013/0089901 A1 | 4/2013 | Seo et al. |

FOREIGN PATENT DOCUMENTS

| | | |
|---|---|---|
| EP | 0831805 A1 | 4/1998 |
| EP | 1506996 A2 | 2/2005 |
| EP | 2337857 A1 | 6/2011 |
| EP | 2391361 A1 | 12/2011 |
| EP | 2405895 A1 | 1/2012 |
| GB | 2379166 A | 3/2003 |
| JP | H08163990 A | 6/1996 |
| JP | H0975000 A | 3/1997 |
| JP | H1072590 A | 3/1998 |
| JP | 2000060587 A | 2/2000 |
| JP | 2006143479 A | 6/2006 |
| JP | 2007143479 | 6/2007 |
| WO | 9428891 A1 | 12/1994 |
| WO | 0149282 A2 | 7/2001 |
| WO | 2005083093 A2 | 9/2005 |
| WO | 2007068997 | 6/2007 |
| WO | 2007069078 | 6/2007 |
| WO | 2008129358 | 10/2008 |
| WO | 2009029793 A1 | 3/2009 |
| WO | 2011139040 | 11/2011 |
| WO | 2012120375 | 9/2012 |
| WO | 2014141098 | 9/2014 |
| WO | 2015179844 A2 | 11/2015 |

OTHER PUBLICATIONS

"Annotated Alignment Noting Applicant's Substitutions", SEQ Id No. 1, Feb. 25, 2021,.
U.S. Appl. No. 15/845,697 , Final Office Action, Mailed on Mar. 2, 2021, 10 pages.
U.S. Appl. No. 15/845,697 , Final Office Action, Mailed on Nov. 26, 2019, 17 pages.
U.S. Appl. No. 15/845,697 , Non-Final Office Action, Mailed on Jul. 22, 2020, 10 pages.
U.S. Appl. No. 15/845,697 , Non-Final Office Action, Mailed on Apr. 18, 2019, 14 pages.
AU2017380721 , "First Examination Report", Sep. 24, 2020, 5 pages.
AU2017380721 , "Second Examination Report", Dec. 18, 2020, 4 pages.
Barclay et al., "Single Cell Oils: Microbial and Algal Oils", Single Cell Oils: Microbial and Algal Oils, 2015, pp. 75-96.
Burja et al., "Isolation and Characterization of Polyunsaturated Fatty Acid producing *Thraustochytrium* Species: Screening of Strains and Optimization of Omega-3 Production", Applied Microbiology and Biotechnology, vol. 72, No. 6, 2006, pp. 1161-1169.
Byreddy et al., "Comparison of Cell Disruption Methods for Improving Lipid Extraction from Thraustochytrid Strains", Marine Drugs, vol. 13, No. 8, Available online at: www.mdpi.com, Aug. 11, 2015, pp. 5111-5127.
Application No. CA3,047,924 , Office Action, Mailed on Jun. 17, 2021, 2 pages.
Application No. CA3, 047,924 , Office Action, Mailed on May 27, 2020, 3 pages.
Chang et al., "Biodiscovery of New Australian Thraustochytrids for Production of Biodiesel and Long-Chain Omega-3 Oils", Applied Microbiology and Biotechnology, vol. 93, No. 5, Mar. 2012, pp. 2215-2231.
Chang et al., "Comparison of *Thraustochytrids aurantiochytrium* Sp., *Schizochytrium* Sp., *Thraustochytrium* Sp., and *Ulkenia* Sp. for Production of Biodiesel, Long-Chain Omega-3 Oils, and Exopolysaccharide,", Marine Biotechnology, vol. 16, No. 4, Aug. 1, 2014, pp. 396-411.

Chang et al., "Improvement of Docosahexaenoic Acid Production on Glycerol by *Schizochytrium* Sp. S31 with Constantly High Oxygen Transfer Coefficient", Bioresource Technology, vol. 142, 2013, pp. 400-406.
Chen et al., "A Novel Feedstock for Biodiesel Production: The Application of Palmitic Acid from Schizochytrium", Energy, vol. 86, Nov. 2015, pp. 128-138.
Chen et al., "Improvement in the Docosahexaenoic Acid Production of *Schizochytrium* Sp. S056 by Replacement of Sea Salt", Bioprocess Biosystems Engineering, vol. 39, No. 2, Feb. 2016, pp. 315-321.
Chen et al., "Transcriptome Analysis Reveals that Up-Regulation of the Fatty Acid Synthase Gene Promotes the Accumulation of Docosahexaenoic Acid in *Schizochytrium* Sp. S056 when Glycerol is Used", Algal Research, vol. 15, 2016, pp. 83-92.
Application No. EP17883535.1 , Extended European Search Report, Mailed on Nov. 27, 2020, 8 pages.
Hong et al., "Production of Lipids Containing High Levels of Docosahexaenoic Acid by a Newly Isolated Microalga, *Aurantiochytrium* sp. KRS101", Applied Biochemistry and Biotechnology, vol. 164, Issue 8, Aug. 2011, pp. 1468-1480.
Hu et al., "The Roles of Different Salts and a Novel Osmotic Pressure Control Strategy for Improvement of DHA Production by *Schizochytrium* Sp.", Bioprocess and Biosystems Engineering, vol. 38, No. 11, Nov. 2015, pp. 2129-2136.
Ling et al., "Impact of Carbon and Nitrogen Feeding Strategy on High Production of Biomass and Docosahexaenoic Acid (DHA) by *Schizochytrium* Sp. Lu310", Bioresource Technology, vol. 184, May 2015, pp. 139-147.
Manikan et al., DNA Data Bank of Japan (DDBJ), Accession No. KF500513, 2013.
Manikan et al., "Identification of Significant Medium Components That Affect Docosahexaenoic Acid Production by *Schizochytrium* sp. SW1", AIP Conference Proceedings, vol. 1571, Dec. 31, 2013, pp. 277-282.
Mo et al., "Development of a PCR Strategy for Thraustochytrid Identification Based on 18S rDNA Sequence", Marine Biology, vol. 140, Issue 5, May 2002, pp. 883-889.
Application No. PCT/IB2017/057974 , International Preliminary Report on Patentability, Mailed on Jul. 4, 2019, 9 pages.
Application No. PCT/IB2017/057974 , International Search Report and Written Opinion, Mailed on Jan. 31, 2018, 14 pages.
Pyle et al., "Producing Docosahexaenoic Acid (DHA)-Rich Algae from Biodiesel-Derived Crude Glycerol: Effects of Impurities on DHA Production and Algal Biomass Composition", Journal of Agricultural and Food Chemistry, vol. 56, 2008, pp. 3933-3939.
Ugalde et al., "Improvement of Culture Conditions for Cell Biomass and Fatty Acid Production by Marine Thraustochytrid F24-2", Journal of Applied Phycology, vol. 30, No. 1, Sep. 15, 2017, pp. 329-339.
Ugalde et al., "Optimization of Culture Conditions for Thraustochytrid F24-2 Biomass Production", Society for Industrial Microbiology and Biotechnology, Aug. 3, 2015, 2 pages.
Ugalde et al., "Screening of Medium Composition and Culture Conditions Affecting Palmitic Acid and Docosahexaenoic Acid (DHA) Production by a Thraustochytrid", Canadian Society for Bioengineering Conference Proceeding, Jul. 3, 2017, pp. CSBE16036.
IN201917026865 , "First Examination Report", Dec. 6, 2021, 6 pages.
Application No. CA3, 047,924 , Office Action, Mailed on May 20, 2022, 3 pages.
Application No. P170103663 , Office Action, Mailed on Feb. 18, 2022, 4 pages.
BR1120190124217 , "Office Action", Dec. 27, 2022, 4 pages.
CN201780079737.9 , "Office Action", Nov. 25, 2022, 7 pages.
EP17883535.1, "Office Action", Sep. 1, 2023, 5 pages.
Bao et al., "Marine Microbiology", China Ocean University Press, Apr. 30, 2008, 6 pages.
CN201780079737.9, "Office Action", Jun. 14, 2023, 8 pages.
CA3,047,924, "Office Action", Mar. 10, 2023, 4 pages.
MX/a/2019/007315, "Office Action", May 3, 2023, 9 pages.
CN201780079737.9, "Office Action", Oct. 28, 2023, 10 pages.
MX/A/2019/007315, "Office Action", Oct. 24, 2023, 14 pages.
Au2022275509, "First Examination Report", Jan. 31, 2024, 4 pages.

(56) References Cited

OTHER PUBLICATIONS

Jiang et al., "Fatty Acid Composition and Squalene Content of the Marine Microalga Schizochytrium mangrovei", Journal of Agricultural and Food Chemistry, vol. 42, No. 5, 2004, pp. 11196-12000.
MX/A/2019/007315, "Office Action", Apr. 5, 2024, 14 pages.
CA3,047,924, "Office Action", Sep. 9, 2024, 5 pages.
EP17883535.1, "Office Action", Sep. 10, 2024, 5 pages.
Huang et al., "Grouping Newly Isolated Docosahexaenoic Acid-Producing Thraustochytrids Based on Their Polyunsaturated Fatty Acid Profiles And Comparative Analysis of 18s Rrna Genes", Marine Biotechnology, vol. 5, Issue 5, Oct. 2003, pp. 450-457.

* cited by examiner

METHODS FOR PRODUCING BIOMASS RICH IN DHA, PALMITIC ACID AND PROTEIN USING A EUKARYOTIC MICROORGANISM

CROSS-REFERENCE TO RELATED APPLICATIONS

This application is a divisional of U.S. application Ser. No. 15/845,697 filed Dec. 18, 2017, which claims priority to U.S. Provisional Application No. 62/437,886, filed Dec. 22, 2016, which is incorporated by reference herein in its entirety.

REFERENCE TO THE SEQUENCE LISTING

The instant application contains a Sequence Listing which has been submitted electronically in ASCII format and is hereby incorporated by reference in its entirety. Said ASCII copy, created on Feb. 15, 2022, is named 095523_1283066_019US2_SL and is 32,933 bytes in size.

BACKGROUND

Fish constitute a large portion of dietary protein and provide essential omega-3 lipids in human diets. Increasing demand is driving growth in seafood markets at an annual rate of 6%. Aquaculture is an integral part of this market as wild catch can no longer satisfy consumer demand. Historically, fish meal (protein) and fish oil (fatty acids, and omega-3 fatty acids in particular) have been used extensively. The growth of aquaculture requires that new, sustainable sources of aquaculture feed, providing carbohydrate, protein and omega-3 fatty acids, be developed. Due to technology limitations, microalgae have been used as a micro-ingredient employed to improve specific properties, not as a macro (protein, oil or carbohydrate) nutrient. Thus, although known to be suitable as a feed component, the use of microalgae is currently limited as a means for addressing sustainability.

BRIEF SUMMARY

Provided herein are eukaryotic microorganisms having a simple lipid profile comprising long chain fatty acids (LCFAs). Also provided are compositions and cultures comprising the eukaryotic microorganisms and heterotrophic medium. Methods of making a lipid composition using the disclosed eukaryotic microorganisms and methods of using lipid compositions by incorporating the lipid compositions into foodstuffs are also provided herein. Also provided are methods of making protein rich biomass using the disclosed microorganisms and optionally incorporating the protein rich biomass into foodstuffs.

DETAILED DESCRIPTION

Figure 1:
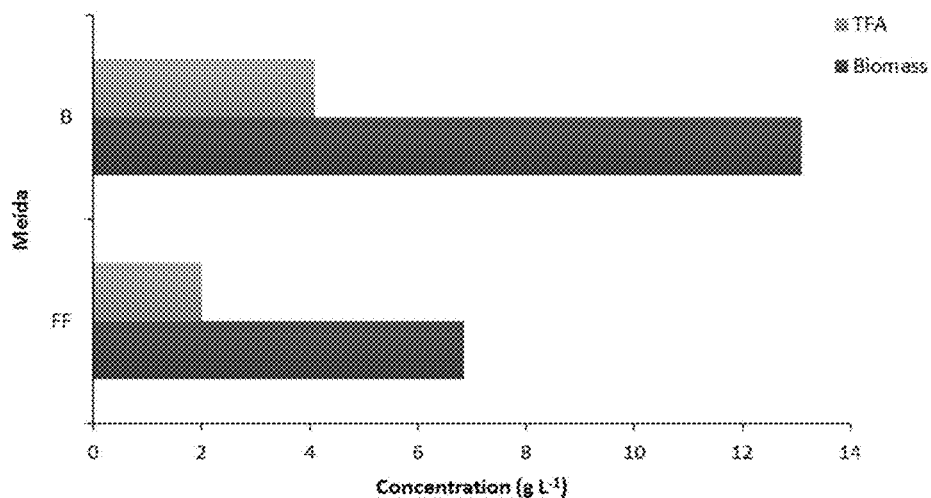
FIG. 1 is a graph showing biomass and TFA production by strain G3-1 in liquid media: basal (B) and full fermentation media (FF).

Microalgae are the primary producers of aquatic ecosystems and represent the origin of essential nutrients (e.g., protein and omega-3 fatty acids), which are metabolized and/or bio-accumulated in the aquatic food chain. As such, high protein and high omega-3 long chain polyunsaturated fatty acid (LC-PUFA) products derived from microalgae have enormous potential to sustainably meet the dietary demands of the rapidly-growing aquaculture sector. Among the large variety of microalgae, the use of heterotrophic microalgae has the greatest potential to provide aquaculture feed inputs that are free from the supply and demand constraints of plant and animal products. Heterotrophic microalgae production requires significantly less land and water, has better process economics, and is independent of environmental conditions (i.e., climate independent). For example, volumetric biomass productivity of heterotrophic microalgae can be two orders of magnitude higher than that of photosynthetic microalgae. The use of heterotrophic microalgae also provides the opportunity to leverage inexpensive and abundant non-food carbon sources converting them directly into high value products through fermentation. Such production processes can also be more easily scaled up, as would be required for an aquaculture feed product.

Provided herein are eukaryotic microorganisms having a simple lipid profile comprising long chain fatty acids (LCFAs). Microorganisms, including Thraustochytrids, produce a variety of lipids including fatty acids in various forms and amounts. As used herein, the term lipid includes phospholipids, free fatty acids, esters of fatty acids, triacylglycerols, sterols and sterol esters, carotenoids, xanthophylls (e.g., oxycarotenoids), hydrocarbons, and other lipids known to one of ordinary skill in the art. Fatty acids are hydrocarbon chains that terminate in a carboxyl group, being termed unsaturated if they contain at least one carbon-carbon double bond, and polyunsaturated when they contain multiple carbon-carbon double bonds. For example, microorganisms can produce (i) short-chain fatty acids (SCFA), which are fatty acids with aliphatic tails of fewer than six carbons (e.g., butyric acid); (ii) medium-chain fatty acids (MCFA), which are fatty acids with aliphatic tails of 6-12 carbons; (iii) long-chain fatty acids (LCFA), which are fatty acids with aliphatic tails 13 to 21 carbons; and very long chain fatty acids (VLCFA), which are fatty acids with aliphatic tails longer than 22 carbons. Various microorganisms produce varying types and amounts of these fatty acids. The specific types and amounts of fatty acids are collectively referred to herein in as the microorganism's lipid profile. Thus, as used herein, the term "lipid profile" refers to the types of lipids and amounts of lipids produced in a microorganism.

As used herein, a "simple lipid profile" refers to a microorganism having 95% or more of the triglycerides in the microorganism being made up of 1, 2, 3, or 4 of the major long chain fatty acids. Optionally, 95%, 96%, 97%, 98%, 99%, or 100% of the triglycerides in the microorganism comprise 1, 2, 3, or 4 of the major long chain fatty acids. Optionally, 95%, 96%, 97%, 98%, 99%, or 100% of the triglycerides in the microorganism comprises myristate (C14:0), palmitic acid (C16:0), docosapentaenoic acid n-6 (C22:5n-6, DPAn6), and docosahexaenoic acid (C22:6n-3, DHA). As used herein, a triglyceride refers to a molecule composed of three fatty acids covalently linked to a glyceride molecule. Thus, the triglyceride fraction of the total fatty acids in the microorganism can be comprised of 95%, 96%, 97%, 98%, 99%, or 100% myristate (C14:0), palmitic acid (C16:0), docosapentaenoic acid n-6 (C22:5n-6, DPAn6), and docosahexaenoic acid (C22:6n-3, DHA).

Long chain fatty acids (LCFA) include, but are not limited to, myristate (C14:0), palmitic acid (C16:0), docosapentaenoic acid n-6 (C22:5n-6, DPAn6), docosahexaenoic acid (C22:6n-3, DHA), lauric acid (C12:0), pentadecylic acid (C15:0), palmitoleic acid (C16:1), margaric acid (C17:0), stearic acid (C18:0), vaccenic acid (C18:1n-7), oleic acid (C18:1n-9), γ-linolenic acid (C18:3n-6), α-linolenic acid (C18:3n-3), stearidonic acid (C18:4), arachidic acid (C20:0), dihomo-γ-linolenic acid (C20:3n-6), arachidonic acid (C20:4n-6, ARA), eicosapentaenoic acid (C20:5n-3, EPA), behenic acid (C22:0), docosatetraenoic acid (C22:4), docosapentaenoic acid n3 (C22:5n-3, DPAn3), and lignoceric acid (C24:0). Optionally, the four major LCFA comprise myristate, palmitic acid, DPA and DHA.

Optionally, the simple lipid profile comprises greater than 3% of each of myristate (C14:0), palmitic acid (C16:0), docosapentaenoic acid n-6 (C22:5n-6, DPAn6), and docosahexaenoic acid (C22:6n-3, DHA). Optionally, the simple lipid profile comprises triglycerides and 95% of the triglycerides are comprised of myristate (C14:0), palmitic acid (C16:0), docosapentaenoic acid n-6 (C22:5n-6, DPAn6), and docosahexaenoic acid (C22:6n-3, DHA). Optionally, the simple lipid profile comprises less than 3% of each of lauric acid (C12:0), pentadecylic acid (C15:0), palmitoleic acid (C16:1), margaric acid (C17:0), stearic acid (C18:0), vaccenic acid (C18:1n-7), oleic acid (C18:1n-9), γ-linolenic acid (C18:3n-6), α-linolenic acid (C18:3n-3), stearidonic acid (C18:4), arachidic acid (C20:0), dihomo-γ-linolenic acid (C20:3n-6), arachidonic acid (C20:4n-6, ARA), eicosapentaenoic acid (C20:5n-3, EPA), behenic acid (C22:0), docosatetraenoic acid (C22:4), docosapentaenoic acid n3 (C22:5n-3, DPAn3), and lignoceric acid (C24:0).

Optionally, the simple lipid profile comprises less than 0.02% short chain fatty acids. Optionally, the simple lipid profile comprises at least 35% C22:6n-3 (DHA) in the triglycerides in the total fatty acids. Optionally, the simple lipid profile comprises 35-40%, 35-45%, 35-50%, 40-45%, 40-50%, or 50%-60% DHA in the triglycerides in the total fatty acids. Stated another way, in the triglyceride fraction of the total fatty acids in the microorganism, the triglycerides can comprise 35-40%, 35-45%, 35-50%, 40-45%, 40-50%, or 50%-60% DHA.

Optionally, the eukaryotic microorganism produces a biomass of at least 20% protein, at least 40% protein, or at least 20-40% protein.

Optionally, the eukaryotic microorganism produces at least about 10% C22:6n-3 (DHA) in the triglycerides in the total fatty acids. Optionally, the eukaryotic microorganism produces at least 30% palmitic acid in the triglycerides in the total fatty acids. Optionally, the eukaryotic microorganism produces at least 40% palmitic acid in the triglycerides in the total fatty acids. Optionally, the eukaryotic microorganism produces one or more carotenoids. Optionally, the one or more carotenoids comprises β-carotene. Optionally, 0-carotene comprises at least 95%, 96%, 97%, 98%, 99%, or 100% of the carotenoids produced in the microorganism.

Disclosed are eukaryotic microorganisms that produce lipids, wherein the eukaryotic microorganism has a simple lipid profile. Optionally, the lipid-producing eukaryotic microorganism has an 18S sequence with at least 97%, 98%, 99% or 100% identity to the sequence set forth in SEQ ID NO:1. Optionally, the eukaryotic microorganism has IDAC Accession No. 220716-01, which was deposited with the International Depositary Authority of Canada (IDAC), National Microbiology Laboratory, Public Health Agency of Canada, 1015 Arlington Street, Winnipeg, Manitoba Canada R3E 3R2, on Jul. 22, 2016, and assigned Accession No. 220716-01. This deposit will be maintained under the terms of the Budapest Treaty on the International Recognition of the Deposit of Microorganisms for the Purposes of Patent Procedure. This deposit is exemplary and was made merely as a convenience for those of skill in the art and is not an admission that a deposit is required for patentability (e.g., under 35 U.S.C. § 112). The terms "G3-1" or "G3-1 strain" or "strain G3-1" are used herein interchangeably to refer to the eukaryotic microorganism deposited with the IDAC and having IDAC Accession No. 220716-01.

The provided microorganisms have distinguishing features over wild type microorganisms in their natural environment. Wild type microorganisms can be found in natural aquatic environments extending from oceanic environments to freshwater lakes and rivers, and also include brackish environments such as estuaries and river mouths. Such environments are not considered to be encompassed by the term heterotrophic medium. The provided microorganisms produce, in a heterotrophic medium, different amounts of one or more lipids and/or protein content from the microorganisms in their natural environment.

Nucleic acid, as used herein, refers to deoxyribonucleotides or ribonucleotides and polymers and complements thereof. The term includes deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, conservatively modified variants of nucleic acid sequences (e.g., degenerate codon substitutions) and complementary sequences can be used in place of a particular nucleic acid sequence recited herein. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The terms identical or percent identity, in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be substantially identical. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A comparison window, as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l. Acad. Sci. USA 85:2444 (1988); by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul et al., Nuc. Acids Res. 25:3389-3402 (1977), and Altschul et al., J. Mol. Biol. 215:403-410 (1990), respectively. BLAST and BLAST 2.0 are used, with the parameters described herein, to determine percent sequence identity for nucleic acids or proteins. Software for performing BLAST analyses is publicly available through the National Center for Biotechnology Information, as known in the art. This algorithm involves first identifying high scoring sequence pairs (HSPs) by identifying short words of a selected length (W) in the query sequence, which either match or satisfy some positive-valued threshold score T when aligned with a word of the same length in a database sequence. T is referred to as the neighborhood word score threshold (Altschul et al.). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The Expectation value (E) represents the number of different alignments with scores equivalent to or better than what is expected to occur in a database search by chance. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, expectation (E) of 10, and the BLOSUM62 scoring matrix (see Henikoff & Henikoff, Proc. Natl. Acad. Sci. USA 89:10915 (1989)), alignments (B) of 50, expectation (E) of 10, M=5, N=−4, and a comparison of both strands.

The term polypeptide, as used herein, generally has its art-recognized meaning of a polymer of at least three amino acids and is intended to include peptides and proteins. However, the term is also used to refer to specific functional classes of polypeptides, such as, for example, desaturases, elongases, etc. For each such class, the present disclosure provides several examples of known sequences of such polypeptides. Those of ordinary skill in the art will appreciate, however, that the term polypeptide is intended to be sufficiently general so as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term polypeptide as used herein. Those in the art can determine other regions of similarity and/or identity by analysis of the sequences of various polypeptides described herein. As is known by those in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

The provided eukaryotic microorganisms can be cultured in a heterotrophic medium. Thus, provided herein are eukaryotic microorganisms having, in a heterotrophic medium, a simple lipid profile comprising long chain fatty acids (LCFAs). Also provided are cultures comprising a lipid-producing eukaryotic microorganism with an 18S sequence, wherein the 18S sequence has at least 98% identity to the sequence set forth in SEQ ID NO:1, and a heterotrophic medium that results in the lipid-producing eukaryotic microorganism having a simple lipid profile comprising long chain fatty acids (LCFAs). Optionally, the simple lipid profile comprises greater than 3% of each of myristic acid (C14:0), palmitic acid (C16:0), docosapentaenoic acid n-6 (C22:5n-6, DPAn6), and docosahexaenoic acid (C22:6n-3, DHA). Optionally, the simple lipid profile comprises less than 3% of each of lauric acid (C12:0), pentadecylic acid (C15:0), palmitoleic acid (C16:1), margaric acid (C17:0), vaccenic acid (C18:1n-11), oleic acid (C18:1n-9), γ-linolenic acid (C18:3n-6), α-linolenic acid (C18:3n-3), stearidonic acid (C18:4), arachidic acid (C20:0), dihomo-γ-linolenic acid (C20:3n-6), arachidonic acid (C20:4n-6, ARA), (C20:3n-3), eicosapentaenoic acid (C20:5n-3, EPA), behenic acid (C22:0), docosatetraenoic acid (C22:4), docosapentaenoic acid n-3 (C22:5n-3, DPAn3), and lignoceric acid (C24:0). Optionally, 95%, 96%, 97%, 98%, 99%, or 100% of the triglycerides in the microorganism comprises myristate (C14:0), palmitic acid (C16:0), docosapentaenoic acid n-6 (C22:5n-6, DPAn6), and docosahexaenoic acid (C22:6n-3, DHA). Optionally, the simple lipid profile comprises less than 0.02% short chain fatty acids. Optionally, the simple lipid profile comprises at least 35% C22:6n-3 (DHA) in the triglycerides in the total fatty acids. Optionally, the heterotrophic medium results in production of at least 20% protein in the whole algae biomass. Optionally, the heterotrophic medium results in production of at least 20 to 40% protein of the biomass. Optionally, the heterotrophic medium results in production of at least about 40% protein. Optionally, the heterotrophic medium further results in production of at least about 10% C22:6n-3 (DHA). Optionally, the heterotrophic medium results in production of at least 30% palmitic acid. Optionally, the heterotrophic medium results in production of at least 40% palmitic acid. Optionally, the heterotrophic medium results in production of one or more carotenoids. Optionally, the one or more carotenoids comprises β-carotene, and wherein the β-carotene comprises at least 95% of total carotenoids. Optionally, β-carotene comprises at least 95%, 96%, 97%, 98%, 99%, or 100% of the carotenoids produced in the microorganism.

The provided microorganisms produce greater than 50% DHA in small fermenters. Optionally, the provided microorganisms produce greater than 50% DHA in 2 liter (L) or 5 liter (L) fermenters. Optionally, the biomass productivity of the microorganism is from 0.5 to 0.8 g/L/h in small fermenters, for example, 2 L or 5 L fermenters. Optionally, the total fatty acid productivity of the microorganism is 0.3 to 0.6 g/L/h in small fermenters, for example, 2 L or 5 L fermenters. Optionally, the DHA productivity of the microorganism is 0.1 to 0.4 g/L/h in small fermenters, for example, 2 L or 5 L fermenters. Optionally, the productivity of C:16 of the microorganism is 0.1 to 0.3 g/L/h in small fermenters, for example, 2 L or 5 L fermenters.

The heterotrophic medium supplies various nutritional components, including a carbon source and a nitrogen source, for the microorganism. Medium for culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine. Optionally, the carbon source is present in the heterotrophic medium at a concentration of less than 60 g/L. Optionally, the carbon source is present in the heterotrophic medium at a concentration of 1 to 60 g/L. Optionally, the carbon source is present in the heterotrophic medium at a concentration of 5 to 60 g/L. Optionally, the carbon source is present in the heterotrophic medium at a concentration of 20 to 40 g/L.

Optionally, the microorganisms can be cultured in medium having a chloride concentration from about 0.5 g/L to about 50.0 g/L. Optionally, microorganisms are cultured in medium having a chloride concentration from about 0.5 g/L to about 35 g/L (e.g., from about 18 g/L to about 35 g/L). Optionally, the microorganisms are cultured in a medium having a chloride concentration from about 2 g/L to about 35 g/L. Optionally, the microorganisms described herein can be grown in low chloride conditions. For example, the microorganisms can be cultured in a medium having a chloride concentration from about 0.5 g/L to about 20 g/L (e.g., from about 0.5 g/L to about 15 g/L). The culture medium optionally includes NaCl. The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. Optionally, the medium comprises 9 g/L chloride when using 20 g/L of carbon, 20 g/L soy peptone, and 5 g/L yeast extract. Optionally, the medium comprises 35 g/L chloride when the medium contains 10 g/L carbon, 5 g/L soy peptone, 5 g/L yeast extract and 10 g/L agar. Optionally, the medium comprises 2 g/L chloride when the medium contains 20-40 g/L carbon, 1 g/L yeast extract, 1-20 g/L monosodium glutamate (MSG), 0.3-2.0 g/L phosphates, 4 g/L magnesium sulfate, 5-10 g/L ammonium sulfate, 1.5 mL/L trace elements solution, 1 mL/L of vitamin B solution, 0.1 g/L $CaCl_2$).

Medium for a Thraustochytrid culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, soy peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L. Optionally, the concentration of nitrogen is in the medium is about 5 to 20 g/L. Optionally, the concentration of nitrogen in the medium is about 10 to 15 g/L. Optionally, the concentration of nitrogen in the medium is about 20 g/L. Optionally, the concentration of nitrogen is about 10 to 15 g/L when yeast extract is the source of complex nitrogen in the medium. Optionally, the concentration of nitrogen is about 1 to 5 g/L when soy peptone is in the medium along with L-Glutamic acid monosodium salt hydrate (MSG) or ammonium sulfate.

The medium optionally includes a phosphate, such as potassium phosphate or sodium-phosphate. Optionally, the culture or heterotrophic medium comprises potassium phosphate monobasic.

Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Optionally, the medium includes at least 1.5 ml/L of a trace element solution. Optionally, the trace element solution comprises 2 mg/mL copper (II)sulfate pentahydrate, 2 mg/mL zinc sulfate heptahydrate, 1 mg/mL cobalt (II) chloride hexahydrate, 1 mg/mL manganese (II) chloride tetrahydrate, 1 mg/mL sodium molybdate dihydrate, 1 mg/mL nickel (II) sulfate.

Optionally, the medium includes magnesium sulfate. Optionally, the heterotrophic medium or culture comprises magnesium sulfate, trace element solution and potassium phosphate monobasic.

Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium can be sterilized.

Optionally, the medium comprises L-Glutamic acid monosodium salt hydrate or monosodium glutamate (MSG). Optionally, the medium comprises 1-20 g/L MSG.

Optionally, the medium comprises 1 g/L MSG when the medium comprises at least 1 g/L yeast extract, 40 g/L carbon, 0.3 g/L KH2PO4, 4 g/L magnesium sulfate and 1.5 mL/L trace elements solution. Optionally, the medium comprises 20 g/L MSG when the medium comprises 5-15 g/L yeast extract, 0-10 g/L ammonium sulfate, 20-40 g/L carbon, 2 g/L chloride, 4 g/L magnesium sulfate, 1.5 mL/L trace elements solution, 0.3-2.0 g/L phosphates, 1 mL/L vitamin solution and 0.1 g/L $CaCl_2$.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar and/or agarose) that provide structural support and/or allow the medium to be in solid form.

Cultivation of the microoganisms can be carried out using known conditions, for example, those described in International Publication Nos. WO 2007/069078 and WO 2008/129358. For example, cultivation can be carried out for 1 to 30 days, 1 to 21 days, 1 to 15 days, 1 to 12 days, 1 to 9 days, or 3 to 5 days. Optionally, cultivation is carried out at temperatures between 4 to 30° C. Optionally, cultivation is carried out by aeration-shaking culture, shaking culture, stationary culture, batch culture, continuous culture, rolling batch culture, wave culture, or the like. Optionally, cultivation is carried out with a dissolved oxygen content of the culture medium between 1 and 20%, between 1 and 10%, or between 1 and 5%.

Provided herein are methods of making a lipid composition. The methods include culturing the provided lipid-producing eukaryotic microorganisms in a heterotrophic medium to produce a simple lipid profile and isolating the lipid composition. Optionally, the lipid-producing eukaryotic microorganism has an 18S sequence, wherein the 18S sequence has at least 98% identity to the sequence set forth in SEQ ID NO:1, and the heterotrophic medium results in the lipid-producing eukaryotic microorganism having a simple lipid profile comprising long chain fatty acids (LCFAs). Optionally, the heterotrophic medium contains less than 3.75 g/L chloride. Optionally, the biomass productivity of the cultured micororganisms is greater than 0.65 g/L/h. Optionally, the triglyceride productivity of the cultured microorganisms is greater than 0.3 g/L/h. Optionally, the heterotrophic medium contains less than 3.75 g/L chloride and the biomass productivity of the cultured micororganisms is greater than 0.65 g/L/h and the triglyceride productivity of the cultured microorganisms is greater than 0.3 g/L/h. Optionally, the simple lipid profile of the microorganism used in the methods of making a lipid composition comprises greater than 3% of each of myristate (C14:0), palmitic acid (C16:0), docosapentaenoic acid n-6 (C22:5n-6, DPAn6), and docosahexaenoic acid (C22:6n-3, DHA). Optionally, the simple lipid profile comprises less than 3% of each of lauric acid (C12:0), pentadecylic acid (C15:0), palmitoleic acid (C16:1), margaric acid (C17:0), stearic acid (C18:0), vaccenic acid (C18:1n-7), oleic acid (C18:1n-9), γ-linolenic acid (C18:3n-6), α-linolenic acid (C18:3n-3), stearidonic acid (C18:4), arachidic acid (C20:0), dihomo-γ-linolenic acid (C20:3n-6), arachidonic acid (C20:4n-6, ARA), eicosapentaenoic acid (C20:5n-3, EPA), behenic acid (C22:0), docosatetraenoic acid (C22:4), docosapentaenoic acid n3 (C22:5n-3, DPAn3), and lignoceric acid (C24:0).

Optionally, the simple lipid profile of the microorganism used in the methods of making a lipid composition comprises less than 0.02% short chain fatty acids. Optionally, the simple lipid profile comprises at least 35% C22:6n-3 (DHA) in the triglycerides in the total fatty acids. Optionally, the simple lipid profile comprises 35-40%, 35-45%, 35-50%, 40-45%, 40-50%, or 50-60% DHA in the triglycerides in the total fatty acids. Optionally, the eukaryotic microorganism as described herein produces a biomass of at least 20% protein. Optionally, the biomass is at least 20 to 40% protein. Optionally, the biomass is at least about 40% protein. Optionally, the eukaryotic microorganism as described herein produces at least about 10% C22:6n-3 (DHA) in the triglycerides in the total fatty acids. Optionally, the eukaryotic microorganism used according to the disclosed methods produces at least 30%, at least 40%, or at least 30-40% palmitic acid in the triglycerides in the total fatty acids.

Optionally, the eukaryotic microorganism produces one or more carotenoids. Optionally, the one or more carotenoids comprises β-carotene. Optionally, 0-carotene comprises at least 95%, 96%, 97%, 98%, 99%, or 100% of the carotenoids produced in the microorganism.

Also provided are methods of making a protein-rich biomass comprising culturing the provided lipid-producing eukaryotic microorganisms in a heterotrophic medium and isolating the protein-rich biomass. Optionally, the method further comprises incorporating the protein-rich biomass into a foodstuff. Optionally, the foodstuff is pet food, a livestock feed, or an aquaculture feed. Optionally, the eukaryotic microorganism as used in the present methods produces a biomass of at least about 20% protein, at least about 40%, or at least about 20 to 40% protein. Optionally, the eukaryotic microorganism produces at least about 10% C22:6n-3 (DHA) in the triglycerides in the total fatty acids.

Optionally, the lipids produced according to the methods described herein can be incorporated into a final product (e.g., a food or feed supplement, an infant formula, a pharmaceutical, a fuel, and the like). Thus, provided is a method of using the lipid composition made according to the methods described herein, wherein the method of use comprises incorporating the lipid composition into a foodstuff.

Further, the provided protein-rich biomass can be incorporated into a final product (e.g., food or feed supplement, biofuel, etc.). Thus, provided is a method of using the protein-rich biomass comprising incorporating the protein-rich biomass into a foodstuff (e.g., a pet food, a livestock feed, or an aquaculture feed).

Suitable food or feed supplements into which the lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFAs) can be incorporated into a nutraceutical or pharmaceutical product. Examples of such a nutraceuticals or pharmaceuticals include various types of tablets, capsules, drinkable agents, etc. Optionally, the nutraceutical or pharmaceutical is suitable for topical application. Dosage forms can include, for example, capsules, oils, granula, granula subtilae, pulveres, tabellae, pilulae, trochisci, or the like.

The oil or lipids produced according to the methods described herein can be incorporated into products in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. Identification and Preliminary Analysis of Thraustochytrid-Like Strain G3-1

After two days of incubation strain G3-1 showed significant accumulation of biomass. In contrast, other thrasutochytrids, under the conditions employed, required at least three days of incubation to achieve a similar level of biomass accumulation. Preliminary analysis also indicated that thraustochytrid-like strain G3-1 was able to accumulate high concentrations of oil rich in docosahexaenoic acid (DHA) and palmitic acid (C16:0). DHA is a fatty acid of high value due to use in human and animal nutrition. Palmitic acid is also of value when employed as a feedstock for biofuel production. Furthermore, with the application of animal nutrition in mind and aquaculture in particular thraustochytrid-like strain G3-1 has been shown to accumulate protein to a level that composes around 30% of its biomass dry weight. Due to these properties thraustochytrid-like strain G3-1 was selected to develop a method to produce biomass rich in DHA, palmitic acid and protein in a short period of time.

Example 2. Evaluation of Strain G3-1 in Two Media Compositions

To evaluate the thraustochytrid-like strain G3-1, it was cultivated under two conditions, full fermentation (FF) media and Basal (B) media. FF media is a complex media and B media is a minimal media used in the analysis and development of different processes, strains and conditions.

A comparison of G3-1 productivity in FF vs B media demonstrated that biomass content was higher in B media with G3-1 producing 53% more biomass (Table 1). Also total fatty acid (TFA) yield increased on a volumetric basis by 49%, owed to higher biomass accumulation. Moreover, on a dry cell weight basis TFA production also increased. In FF media fatty acids composed 289 mg g$^{-1}$ biomass while in B media this increased to 312 mg g$^{-1}$ biomass, an increase of 8% (Table 1). The obtained results suggest that strain G3-1 may be sensitive to the osmotic pressure imposed high concentration of glucose in FF media. Protein content was also analyzed revealing that up to 30% of dry cell weight is attributed to protein.

Experimental Details

Growth and cultivation—Seed cultures were produced by either adding 1 mL of the ASW containing pure strain G3-1 culture or two loops of pure colonies taken from an agar plate, to 30 mL aliquots of B media in 150 mL baffled Erlenmeyer flasks. Flasks were incubated at 25° C. and 200 rpm for 2 days. 5 mL aliquots of seed cultures (previously adjusted with sterile fresh B media to OD600 nm=1.5) were taken under aseptic conditions and added to 95 mL of sterile test media in 500 mL Erlenmeyer flasks. Test media composition and culture conditions for these flasks were evaluated using a B media (described above) and FF media, which was composed of 60 g L$^{-1}$ glucose, 2 g L$^{-1}$ sea salt, 4 g L$^{-1}$ soy peptone, 1 g L$^{-1}$ yeast extract, 4 g L$^{-1}$ magnesium sulfate, 2 g L$^{-1}$ sodium chloride, 5 mg L$^{-1}$ ferric chloride, 3 mg L$^{-1}$ copper sulfate, 2 mg L$^{-1}$ sodium molybdate, 3 mg L$^{-1}$ zinc sulfate, 2 mg L$^{-1}$ cobalt (II) chloride, 2 mg L$^{-1}$ manganese chloride, 2 mg L$^{-1}$ nickel sulfate, 1.6 g L$^{-1}$ potassium phosphate monobasic, 1.75 g L$^{-1}$ potassium phosphate dibasic, 6.8 g L$^{-1}$ ammonium sulfate, 0.1 g L$^{-1}$ calcium chloride dehydrate, 0.01 g L$^{-1}$ cobalamin, 0.01 g L$^{-1}$ biotin and 2 g L$^{-1}$ thiamin hydrochloride. After two days of fermentation, broth samples were taken from each flask and cells were harvested by centrifugation at 4150 rpm for 20 min at 2° C. The pellet was rinsed with distilled water to remove the salts and residual substrate, and then re-centrifuged. Pellets were frozen at −80° C., freeze-dried and stored at −20° C. prior to biomass and fatty acid analysis. The freeze-dried cell pellets were weighed to determine the biomass of strain G3-1 culture and reported as dry weight of cells per unit volume of media (g L$^{-1}$). A direct one step transesterification method was carried out to prepare fatty acid methyl esters (FAMEs) from freeze-dried biomass to estimate the oil content inside the cells. FIG. 1 demonstrates that media composition had a significant effect (p<0.05) on biomass and TFA production by G3-1. See also Table 1.

TABLE 1

Biomass and TFA production by strain G3-1 in liquid media.

| Media | Biomass (g L$^{-1}$) | TFA (g L$^{-1}$) |
| --- | --- | --- |
| Full fermentation (FF) | 6.9 ± 0.3 | 2.0 ± 0.1 |
| Basal (B) | 13.1 ± 0.3 | 4.1 ± 0.3 |

Figure 2:
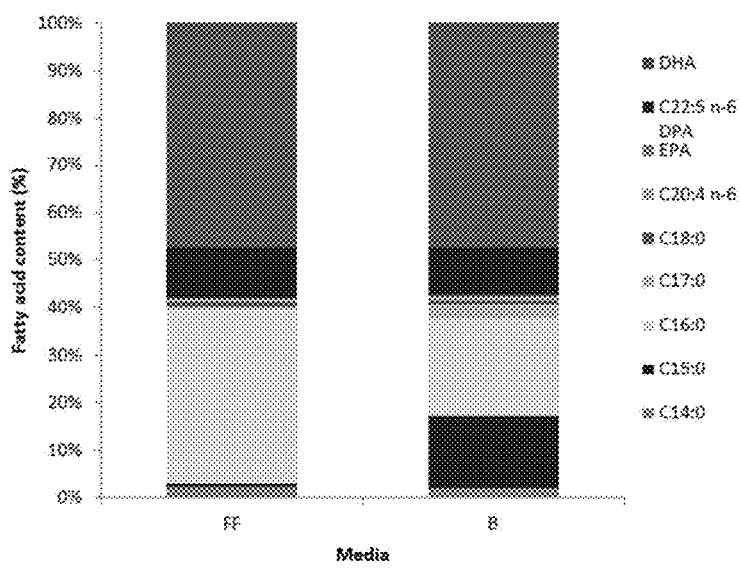
FIG. 2 is a graph showing the effect of media composition on fatty acid profile of the intracellular oil of strain G3-1: basal (B), full fermentation media (FF).

This investigation also demonstrated that media composition was able to modify the fatty acid profile of the oil produced by G3-1 (FIG. 2). When G3-1 was cultured in B media, the composition of fatty acids slightly changed compared to FF media. However, DHA was still produced at high a concentration, G3-1 produced DHA at 47.1% and 46.9% of total fatty acid content, when cultured in FF and B media, respectively. See Table 2.

TABLE 2

Effect of media composition on fatty acid profile of the intracellular oil of strain G3-1: basal (B), full fermentation media (FF).

| Fatty acids | FF mg/g | B mg/g | FF % | B % |
| --- | --- | --- | --- | --- |
| C14:0 | 6.4 ± 0.4 | 6.6 ± 0.4 | 2.2 ± 0.0 | 2.1 ± 0.0 |
| C15:0 | 2.3 ± 0.1 | 47.1 ± 0.7 | 0.8 ± 0.1 | 15.1 ± 0.9 |
| C16:0 | 105.2 ± 6.6 | 63.1 ± 4.5 | 36.7 ± 0.3 | 20.1 ± 0.6 |
| C17:0 | 1.0 ± 0.1 | 9.5 ± 0.1 | 0.4 ± 0.0 | 3.0 ± 0.1 |
| C18:0 | 3.2 ± 0.2 | 1.9 ± 0.1 | 1.1 ± 0.0 | 0.6 ± 0.0 |
| C20:4-6 | 1.2 ± 0.3 | 2.2 ± 0.1 | 0.4 ± 0.1 | 0.7 ± 0.0 |
| EPA | 1.1 ± 0.3 | 0.8 ± 0.0 | 0.4 ± 0.1 | 0.3 ± 0.0 |
| C22:5 n-6 DPA | 29.8 ± 1.9 | 31.0 ± 1.4 | 10.4 ± 0.1 | 9.9 ± 0.0 |
| DHA | 134.9 ± 9.4 | 146.9 ± 7.4 | 47.1 ± 0.2 | 46.9 ± 0.3 |
| TFA | 285.1 | 309.1 | | |

Figure 3:
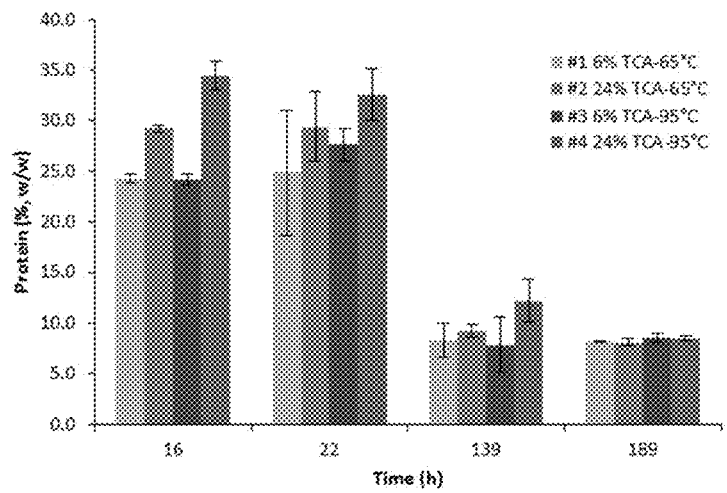
FIG. 3 is a graph showing the effect of hot-TCA treatments on the efficiency of protein extraction (protein content as %) in lyophilized G3-1 biomass from early exponential (T16h and T22h) and stationary phase (T139h and T189h).

To analyze the protein content of strain G3-1 biomass a hot-TCA method was adapted from the literature and optimized using G3-1 culture aged at 16 h and 22 h. Four combinations of hot-TCA conditions were evaluated and the resultant protein content is shown in FIG. 3. Using condition 4 over 30% protein content was detected in G3-1, revealing the potential of this strains to produce meaningful amounts of protein (i.e., >40%) and therefore could serve as a partial fish meal replacement product.

Example 3. Nutritional Requirements for Enhanced Biomass Production and Lipid Accumulation by Thraustochytrid-Like Strain G3-1

Previous analysis comparing FF and B media demonstrated that the nutritional requirements of G3-1 differ to those of other thrasutochytrids. A series of experiments were designed to better understand what aspects of B media affect growth and lipid production for G3-1. To do this, a standard factorial design experimental approach was applied, also called a Plackett-Burman.

The results show that the nutrient requirements of strain G3-1 differ from those of other thraustochytrids, that G3-1 has the capacity to produce short chain saturated fatty acids (palmitic acid) and long chain polyunsaturated fatty acids (DHA), likely through independent pathways, a classic elongation and desaturation pathway plus an independent polyketide synthase pathway. They also demonstrate that soy peptone and sea salt together have a significant impact on G3-1 productivity.

Experimental Details

An irregular fraction factorial design (2^4*3/4) was used to explore the significance of four independent variables, B media components, on biomass and fatty acid production. Independent variables were tested at a high (+1) and low (−1) concentrations (Table 3). A total of twelve experimental runs were completed in duplicate, as described in Table 4.

TABLE 3

Independent variables and their levels used in the irregular fraction factorial design.

| Variables | Coded Xi | Coded level −1 | Coded level +1 |
|---|---|---|---|
| Glucose (g L$^{-1}$) | X1 | 20 | 40 |
| Soy peptone (g L$^{-1}$) | X2 | 4 | 20 |
| Yeast extract (g L$^{-1}$) | X3 | 1 | 5 |
| Sea salt (g L$^{-1}$) | X4 | 2 | 9 |

TABLE 4

Irregular fraction factorial design matrix.

Figure 4:
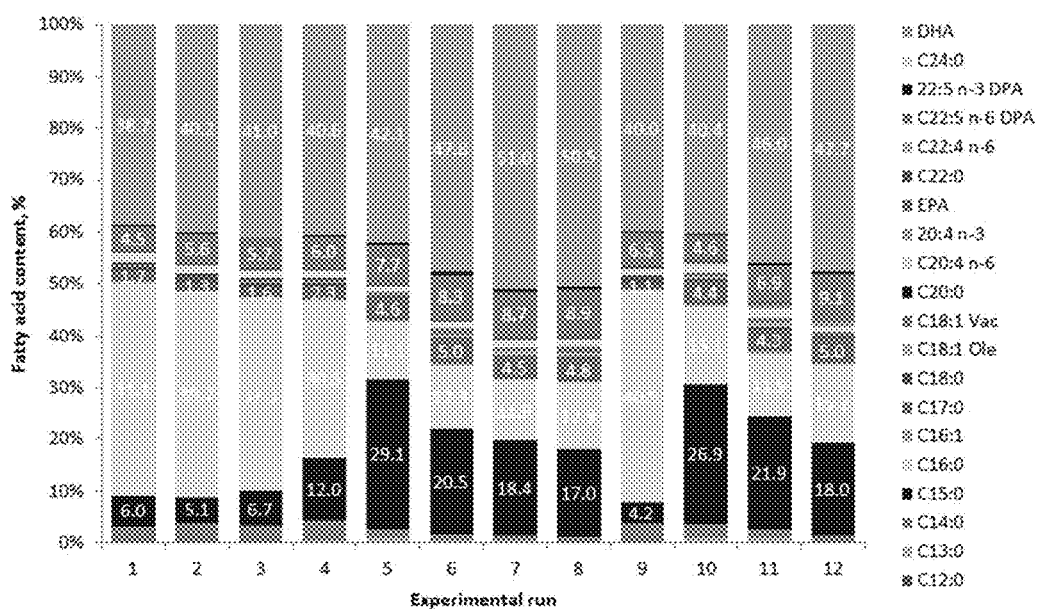
FIG. 4 is a graph showing the fatty acid profile of the intracellular oil of strain G3-1 under different liquid media compositions.

| Run | Block | Coded Variable X1 | X2 | X3 | X4 | Process Variable X1 | X2 | X3 | X4 |
|---|---|---|---|---|---|---|---|---|---|
| 1 | 1 | −1 | −1 | −1 | −1 | 20 | 4 | 1 | 2 |
| 2 | 1 | −1 | −1 | −1 | +1 | 20 | 4 | 1 | 9 |
| 3 | 1 | −1 | −1 | +1 | −1 | 20 | 4 | 5 | 2 |
| 4 | 1 | −1 | −1 | +1 | +1 | 20 | 4 | 5 | 9 |
| 5 | 1 | −1 | +1 | −1 | −1 | 20 | 20 | 1 | 2 |
| 6 | 1 | −1 | +1 | −1 | +1 | 20 | 20 | 1 | 9 |
| 7 | 1 | −1 | +1 | +1 | −1 | 20 | 20 | 5 | 2 |
| 8 | 1 | −1 | +1 | +1 | +1 | 20 | 20 | 5 | 9 |
| 9 | 1 | +1 | −1 | −1 | +1 | 40 | 4 | 1 | 9 |
| 10 | 1 | +1 | −1 | +1 | −1 | 40 | 4 | 5 | 2 |
| 11 | 1 | +1 | +1 | −1 | −1 | 40 | 20 | 1 | 2 |
| 12 | 1 | +1 | +1 | +1 | +1 | 40 | 20 | 5 | 9 | interaction between soy peptone and sea salt concentration (X2*X4) had a significant effect (p<0.05) on the ability of G3-1 to produce biomass. Additionally, the amount of intracellular fatty acids accumulated by strain G3-1 was significantly (p<0.05) affected by soy peptone (X2), yeast extract (X3) and sea salt concentration (X4), and the interaction between glucose and sea salt concentration (X1*X4). In addition to affecting biomass and lipid productivity, fatty acid profile was also influenced by the changes imposed (FIG. 4). Broadly speaking, high amounts of DHA, 47.7 to 51.0% of TFA, were synthesized by G3-1 cells in this experiment for the following the combination of ingredients for runs 6, 7, 8 and 12 (in Table 4). Thus, G3-1 has the metabolic capacity to easily produce biomass composed of >50% DHA. Equally important, this series of experiments identified conditions that result in the production of lower amounts of saturated fatty acids, and affected overall productivity (Table 5, FIG. 4). The composition of the liquid media selected to increase biomass production, TFA yield and DHA by strain G3-1 at a lab scale was 20 g L$^{-1}$ glucose, 20 g L$^{-1}$ soy peptone, 5 g L$^{-1}$ yeast extract and 9 g L$^{-1}$ sea salts. This is the same as the previously described Basal (B) media.

TABLE 5

Fatty acid profile of the intracellular oil of strain G3-1 under the different liquid media compositions tested using an irregular fraction factorial design.

| | Fatty Acids (%) | | | | | | | | | |
|---|---|---|---|---|---|---|---|---|---|---|
| Run | C14:0 | C15:0 | C16:0 | C16:1 | C17:0 | C18:0 | C18:1 Ole | C18:1 Vac | C20:0 | C20:4 n-6 |
| 1 | 2.9 | 6 | 41.1 | 0.3 | 1.7 | 1.1 | 0.1 | 0.4 | 0.2 | 1.7 |
| 2 | 3.6 | 5.1 | 39.7 | 0.3 | 1.3 | 1.1 | 0.1 | 0.4 | 0.3 | 1.6 |
| 3 | 3 | 6.7 | 37.3 | 0.3 | 1.6 | 1 | 0.2 | 0.5 | 0.2 | 1.4 |
| 4 | 3.9 | 12 | 30.5 | 0.3 | 2.3 | 0.9 | 0.2 | 0.5 | 0.2 | 1.4 |
| 5 | 1.7 | 29.1 | 11.1 | 0.2 | 4.6 | 0.3 | 0.3 | 0.3 | 0 | 1 |
| 6 | 1.2 | 20.5 | 12.3 | 0.2 | 5 | 0.3 | 0.5 | 1.1 | 0 | 1.3 |
| 7 | 1 | 18.4 | 11.9 | 0 | 4.5 | 0.1 | 0.7 | 0.9 | 0 | 1.4 |
| 8 | 1.1 | 17 | 12.9 | 0 | 4.8 | 0.2 | 0.6 | 1.2 | 0 | 1.4 |
| 9 | 3.5 | 4.2 | 40.9 | 0.2 | 1.1 | 1.1 | 0.1 | 0.3 | 0.2 | 1.1 |
| 10 | 2.8 | 26.9 | 15.1 | 0.4 | 4.4 | 0.4 | 0.4 | 0.9 | 0 | 1.7 |
| 11 | 1.9 | 21.9 | 11.9 | 0.5 | 4.3 | 0.4 | 0.7 | 1.1 | 0 | 1.7 |
| 12 | 1.2 | 18 | 15.2 | 0 | 5 | 0.5 | 0.3 | 0.5 | 0 | 0.9 |

| | Fatty Acids (%) | | | | | | | |
|---|---|---|---|---|---|---|---|---|
| Run | EPA | C22:5 n-6 DPA | DHA | SFA | MUFA | PUFA | Biomass (g/L) | TFA (g/L/d) |
| 1 | 0.5 | 4.5 | 38.7 | 53 | 0.8 | 45.4 | 5.1 ± 0.09 | 2.26 ± 0.08 |
| 2 | 0.5 | 5.6 | 40.2 | 51.1 | 0.8 | 47.9 | 5.7 ± 0.12 | 2.59 ± 0.04 |
| 3 | 0.4 | 5.7 | 41 | 49.8 | 1 | 48.5 | 5.3 ± 1.00 | 1.82 ± 0.34 |
| 4 | 0.5 | 6 | 40.6 | 49.8 | 1 | 48.5 | 5.9 ± 0.12 | 1.89 ± 0.06 |
| 5 | 0.4 | 7.7 | 42.1 | 46.8 | 0.8 | 51.2 | 7.6 ± 0.43 | 1.27 ± 0.06 |
| 6 | 0.6 | 8.3 | 47.8 | 39.3 | 1.8 | 58 | 6.0 ± 0.50 | 0.64 ± 0.08 |
| 7 | 0.6 | 8.7 | 51 | 35.9 | 1.6 | 61.7 | 7.2 ± 0.85 | 0.71 ± 0.04 |
| 8 | 0.7 | 8.9 | 50.5 | 36 | 1.8 | 61.5 | 6.6 ± 1.05 | 0.69 ± 0.11 |
| 9 | 0.4 | 6.5 | 40 | 51 | 0.6 | 48 | 5.8 ± 0.69 | 3.02 ± 0.47 |
| 10 | 0.8 | 4.6 | 40.4 | 49.6 | 1.7 | 47.5 | 5.0 ± 0.66 | 0.90 ± 0.13 |
| 11 | 0.8 | 6.9 | 46 | 40.4 | 2.3 | 55.4 | 6.8 ± 0.81 | 0.68 ± 0.07 |
| 12 | 0.5 | 9.1 | 47.7 | 39.9 | 0.8 | 58.2 | 7.8 ± 0.27 | 0.90 ± 0.02 |

Example 4. Evaluation of Thraustochytrid-Like Strain G3-1 in Lab Fermenters

Basal (B) media formulation from run 8, described above, was selected to carry out fermentations using 2 L fermenters to evaluate the potential of the strain G3-1 to produce biomass rich in DHA and palmitic acid.

In an 88 hour fermentation thraustochytrid-like strain G3-1 produced 51.8 g L$^{-1}$ biomass composed of 67.3% TFA. DHA and palmitic acid constituted 38.8% and 44.7% of TFA, respectively. TFA productivity was 0.398 g L$^{-1}$ hr$^{-1}$ which exceeded published examples by >32%.

Experimental Details

G3-1 was pre-cultured in Erlenmeyer flasks containing 500 mL of liquid media (20 g L$^{-1}$ glucose, 20 g L$^{-1}$ soy peptone, 5 g L$^{-1}$ yeast extract and 9 g L$^{-1}$ sea salts). Flasks were incubated under agitation at 25° C. and 200 rpm for 2 days. After the incubation period, 200 mL of the pre-culture was transferred into 1.8 L of the same media, in a 2-L fermentation vessel. Batch culture conditions were applied as follows: 25° C., agitation starting at 400 rpm and reaching 600 rpm, aeration at 0.3 VVM with atmospheric air, and pH 6.8. Cells were collected at 10-15 h intervals and growth, oil (TFA) and DHA content examined.

Figure 5:
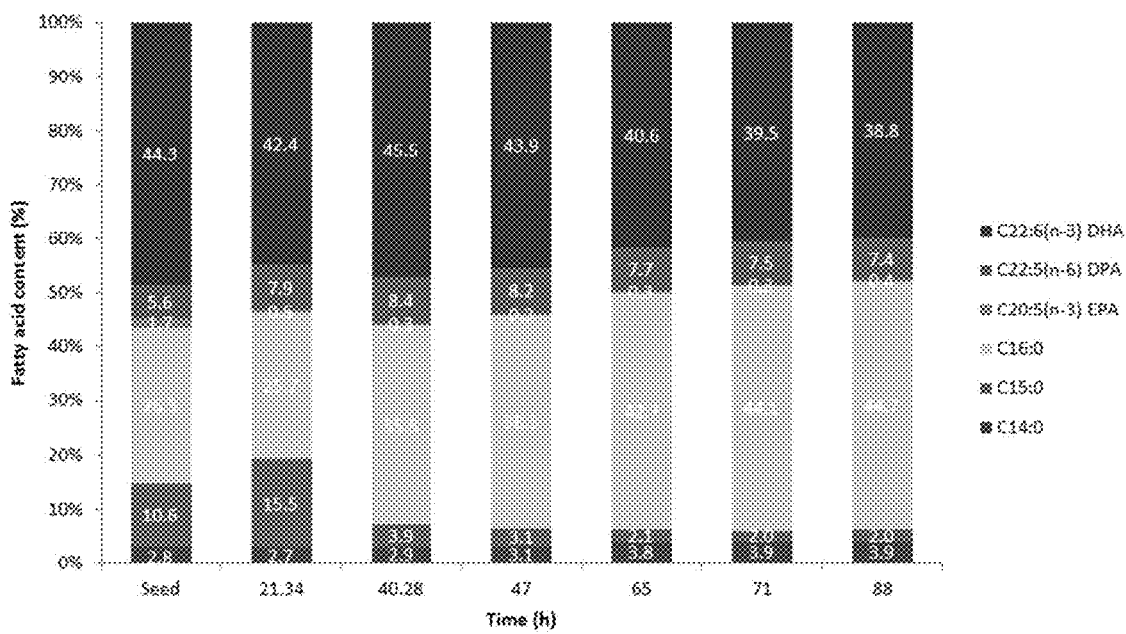
FIG. 5 is a graph showing the fatty acid profile of the intracellular oil of strain G3-1. Cells were cultured in 2-L fermenters using a selected basal media.

Glucose in the media was completely consumed after 20 h of fermentation. Fed-batch cultures were carried out for a total of 88 h. After 65 h of fed-batch fermentation, G3-1 produced 34.7 g L$^{-1}$ of biomass and 77.1% TFA. DHA (40.6%) and palmitic acid (42.7%) where the main fatty acids found in the lipid produced by this strain. After 88 h of fermentation, the total biomass accumulated was 51.8 g L$^{-1}$. At the end of the fermentation, 88 hours, dry biomass, TFA and DHA measured 51.8 g L$^{-1}$, 70% and 38.8%, respectively. Thus, for this fermentation total fatty acid productivity was 0.396 g L$^{-1}$ h$^{-1}$ and DHA productivity was 0.154 g L$^{-1}$ h$^{-1}$. Table 6 and FIG. 5 presents the fatty acid profile of G3-1 when cultured under the described fermentation conditions. As a starting point with minimal process optimization G3-1 is considered a very high DHA production strain.

TABLE 6

Oil production and fatty acid profile of the intracellular oil of strain G3-1. Cells were cultured in 2-L fermenters using a selected basal media.

| Time | TFA | | | | | Fatty acids (%) C20:5 (n-3) | C22:5 (n-6) | C22:6 (n-3) | Biomass | TFA | Productivity (g L$^{-1}$ h$^{-1}$) | | | |
|---|---|---|---|---|---|---|---|---|---|---|---|---|---|---|
| (h) | (%) | C14:0 | C15:0 | C16:0 | C18:0 | EPA | DPA | DHA | (g/L) | (mg/g) | Biomass | TFA | DHA | C16:0 |
| Seed | 19.6 | 2.8 | 10.6 | 26.3 | 0.9 | 1.7 | 5.6 | 44.3 | 13.1 | 196.3 | | | | |
| 21.34 | 24.0 | 2.7 | 15.5 | 25.7 | 0.8 | 0.5 | 7.9 | 42.4 | 14.7 | 240.2 | | | | |
| 40.28 | 49.5 | 2.9 | 3.9 | 35.8 | 1.0 | 0.3 | 8.4 | 45.5 | 28.1 | 495.4 | | | | |
| 47 | 55.6 | 3.1 | 3.1 | 38.3 | 1.1 | 0.3 | 8.2 | 43.9 | 34.8 | 555.7 | | | | |
| 65 | 77.1 | 3.8 | 2.1 | 42.7 | 1.1 | 0.3 | 7.7 | 40.6 | 34.7 | 770.9 | | | | |
| 71 | 74.2 | 3.9 | 2.0 | 44.1 | 1.1 | 0.3 | 7.5 | 39.5 | 36.9 | 742.0 | | | | |
| 88 | 67.3 | 3.9 | 2.0 | 44.7 | 1.1 | 0.4 | 7.4 | 38.8 | 51.8 | 672.6 | 0.589 | 0.396 | 0.154 | 0.177 |

Example 5. Improving the Process Through the Use of a Modified Full Fermentation Media In order to achieve higher biomass productivity, the effect of a modified full fermentation (MFF) media was assessed for impact on biomass and fatty acid accumulation with respect to strain G3-1. The modified fermentation (MFF) media is a complex media rich in minerals and vitamins that is identical to that employed previously, i.e., FF, except that glucose was reduced from 60 g L$^{-1}$ to 20 g L$^{-1}$ to reduce osmotic pressure. 2 L fed-batch fermentations were carried out and changes in biomass and fatty acid content monitored. In this 115 hour fermentation thraustochytrid-like strain G3-1 produced 85.4 g L$^{-1}$ biomass composed of 63.6% TFA. DHA and palmitic acid constituted 43.4% and 41.0% of TFA, respectively. TFA productivity was 0.471 g L$^{-1}$ h$^{-1}$, which exceeded published examples by >56%.

Experimental Details

Figure 6:
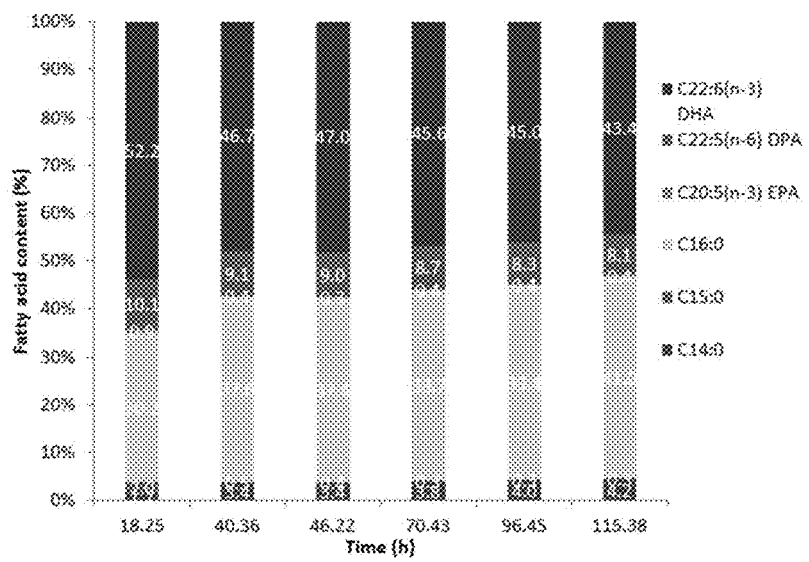
FIG. 6 is a graph showing the fatty acid profile of the intracellular oil of strain G3-1. Cells were cultured in 2-L fermenters using a modified full fermentation media.

A modified full fermentation media (MFF) was used to culture strain G3-1 in a 2-L fermenter for enhanced biomass and fatty acid production. G3-1 was pre-cultured in Erlenmeyer flasks containing 500 mL of the selected basal media (20 g L$^{-1}$ glucose, 20 g L$^{-1}$ soy peptone, 5 g L$^{-1}$ yeast extract and 9 g L$^{-1}$ sea salts). Flasks were incubated under agitation at 25° C. and 200 rpm for 2 days. After the incubation period, 200 mL of the pre-cultured cells were transferred into 1.8 L of MFF media (20 g L$^{-1}$ glucose, 2 g L$^{-1}$ sea salt, 4 g L$^{-1}$ soy peptone, 1 g L$^{-1}$ yeast extract, 4 g L$^{-1}$ magnesium sulfate, 2 g L$^{-1}$ sodium chloride, 5 mg L$^{-1}$ ferric chloride, 3 mg L$^{-1}$ copper sulfate, 2 mg L$^{-1}$ sodium molybdate, 3 mg L$^{-1}$ zinc sulfate, 2 mg L$^{-1}$ cobalt (II) chloride, 2 mg L$^{-1}$ manganese chloride, 2 mg L$^{-1}$ nickel sulfate, 1.6 g L$^{-1}$ potassium phosphate monobasic, 1.75 g L$^{-1}$ potassium phosphate dibasic, 6.8 g L$^{-1}$ ammonium sulfate, 0.1 g L$^{-1}$ calcium chloride dehydrate, 0.01 g L$^{-1}$ cobalamin, 0.01 g L$^{-1}$ biotin and 2 g L$^{-1}$ thiamin hydrochloride) and batch cultured in 2-L fermenters under the conditions of 25° C., agitation starting at 450 rpm and reaching 500 rpm, aeration at 0.3 VVM with atmospheric air, and pH 6.8. Cells were collected at 10-15 hr intervals and the biomass, TFA and DHA were measured. Glucose in the media was completely consumed after 18-20 h of fermentation and at that time. The culture was then batch fed with 75% (w/v) glucose, until 115.38 h when the fermentation was ended. At the end of the fermentation (115.38 h) biomass, TFA and DHA measured 85.4 g L$^{-1}$, 63.6% and 43.4% DHA (Table 7, FIG. 6). For this fermentation productivity for biomass, TFA and DHA was 0.740 g L$^{-1}$ h$^{-1}$, 0.471 g L$^{-1}$ h$^{-1}$ and 0.204 g L$^{-1}$ h$^{-1}$, respectively. The oil obtained under these conditions was high in DHA.

TABLE 7

Oil production and fatty acid profile of the intracellular oil of MARA G3-1. Cells were cultured in 2-L fermenters using a modified full fermentation media.

| Time | TFA | | | | | Fatty Acids (%) C20:5 (n-3) | C22:5 (n-6) | C22:6 (n-3) | Biomass | TFA | Productivity (g/L/h) | | | |
|---|---|---|---|---|---|---|---|---|---|---|---|---|---|---|
| (h) | (%) | C14:0 | C15:0 | C16:0 | C18:0 | EPA | DPA | DHA | (g/L) | (mg/g) | Biomass | TFA | DHA | C16:0 |
| 18.25 | 13.8 | 1.7 | 2.0 | 30.2 | 0.8 | 0.9 | 10.1 | 52.2 | 16.6 | 137.5 | | | | |
| 40.36 | 46.2 | 3.4 | 0.5 | 37.6 | 1.0 | 0.4 | 9.1 | 46.7 | 42.0 | 462.3 | | | | |
| 46.22 | 50.1 | 3.4 | 0.4 | 37.4 | 1.0 | 0.3 | 9.0 | 47.0 | 49.3 | 501.1 | | | | |
| 70.43 | 60.3 | 3.8 | 0.3 | 38.7 | 1.0 | 0.4 | 8.7 | 45.6 | 67.5 | 603.1 | | | | |
| 96.45 | 66.0 | 4.0 | 0.3 | 39.4 | 1.0 | 0.4 | 8.3 | 45.0 | 80.4 | 659.9 | | | | |
| 115.38 | 63.6 | 4.2 | 0.3 | 41.0 | 1.0 | 0.4 | 8.1 | 43.4 | 85.4 | 636.3 | 0.740 | 0.471 | 0.204 | 0.193 |

Biomass production was successfully enhanced when an MFF media was used to culture G3-1 in 2 L-fermenters. However, after 115.38 h of fed-batch fermentation TFA reached 63.6% of biomass dry weight. A possible explanation for this is that MFF contained less soy peptone and sea salt than B media. Components that were found to be important in the initial factorial design experiment.

Example 6. The Effect of Nitrogen Limitation on the Oil Accumulation by Thraustochytrid-Like Strain G3-1

The modified full fermentation media (MFF), described above, was adjusted to reduce the concentration of inorganic nitrogen (in the form of ammonium sulphate) in the liquid media by 50%. Strain G3-1 was cultured in 2 L-fermenters. Glucose consumption was monitored and, when the cells showed signs of starvation, fermentations were fed-batch with 75% (w/v) glucose.

In this 112 hour fermentation, thraustochytrid-like strain G3-1 produced 79.5 g $L^{-1}$ biomass composed of 77.4% TFA. DHA and palmitic acid constituted 36.9% and 48.2% of TFA, respectively. TFA productivity was 0.548 g $L^{-1}$ $h^{-1}$, which exceeds published examples by >82%.

Experimental Details

G3-1 was pre-cultured following the same conditions described previously. 200 mL of pre-cultured cells were transferred to 1.8 L MFF media with half the normal amount of inorganic nitrogen (2-L vessel fermenter). Media was formulated using 3.4 g $L^{-1}$ of ammonium sulphate and all the other ingredients were maintained at the same concentration as described previously. Culture conditions were 25° C., agitation started at 480 rpm and increased 500 rpm over the course of the fermentation, aeration was maintained at 0.3 VVM with atmospheric air, and pH 6.8 was maintained. Cells were collected at 10-15 hr intervals and biomass, TFA and DHA contents were analysed.

Figure 7:
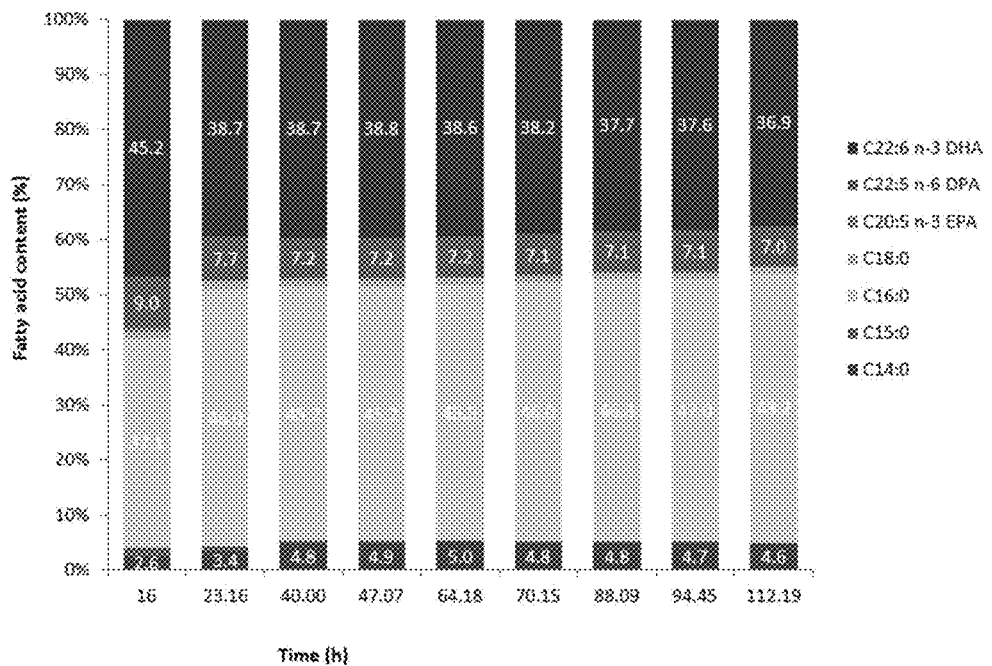
FIG. 7 is a graph showing the fatty acid profile of the intracellular oil of strain G3-1. Cells were cultured in 2-L fermenters using half concentration of ammonium sulphate in a modified full fermentation media.

FIG. 7 shows that using half of the concentration of ammonium sulphate in MFF media accelerated the rate of palmitic acid (C16:0) production by the employed strain. At 40 h, nitrogen was exhausted. The data in Table 8 shows that both biomass and TFA continued to accumulate in the G3-1 culture. It is also apparent that little change in the TFA profile occurred after nitrogen limitation (FIG. 7).

In this investigation, TFA increased from 18.3 to 75.9% (maximally) of dry cell weight, as a percentage of TFA palmitic acid increased from around 45% to 48% over the course of the fermentation. Over the same time period DHA reduced slightly from 45% to 36.9% (Table 8). This corresponds to the biosynthesis of 372.7 mg $g^{-1}$ palmitic acid and 285.3 mg $g^{-1}$ DHA. Production rate for these two fatty acids is 0.264 g $L^{-1}$ $h^{-1}$ palmitic acid and 0.202 g $L^{-1}$ $h^{-1}$ DHA.

The observed increase in palmitic acid biosynthesis is not surprising because nitrogen stress is known to induce the expression of genes in the classic fatty acid synthesis pathway responsible for palmitic acid production. However, it is reassuring to see that DHA production remains approximately the same irrespective of nitrogen stress.

TABLE 8

Oil production and fatty acid profile of the intracellular oil of strain G3-1. Cells were cultured in 2-L fermenters using half concentration of ammonium sulphate in a modified full fermentation media.

| Time | TFA | Fatty acids (%) | | | | C20:5 (n-3) | C22:5 (n-6) | C22:6 (n-3) | Biomass | TFA | Productivity (g/L/h) | | | |
|---|---|---|---|---|---|---|---|---|---|---|---|---|---|---|
| (h) | (%) | C14:0 | C15:0 | C16:0 | C18:0 | EPA | DPA | DHA | (g/L) | (mg/g) | Biomass | TFA | DHA | C16:0 |
| 16 | 18.3 | 2.6 | 1.2 | 37.1 | 1.0 | 0.7 | 9.0 | 45.2 | 16.41 | 183.5 | | | | |
| 23.16 | 37.7 | 3.4 | 0.7 | 46.0 | 1.2 | 0.4 | 7.7 | 38.7 | 23.7 | 376.9 | | | | |
| 40.00 | 59.0 | 4.8 | 0.4 | 45.2 | 1.1 | 0.3 | 7.2 | 38.7 | 37.8 | 589.8 | | | | |
| 47.07 | 62.5 | 4.9 | 0.4 | 45.2 | 1.1 | 0.3 | 7.2 | 38.8 | 44.0 | 624.6 | | | | |
| 64.18 | 70.1 | 5.0 | 0.3 | 45.5 | 1.1 | 0.3 | 7.2 | 38.6 | 55.9 | 700.8 | | | | |
| 70.15 | 73.1 | 4.8 | 0.3 | 46.0 | 1.1 | 0.3 | 7.1 | 38.2 | 58.5 | 730.9 | | | | |
| 88.09 | 73.8 | 4.8 | 0.2 | 46.8 | 1.1 | 0.3 | 7.1 | 37.7 | 70.0 | 738.0 | | | | |
| 94.45 | 75.9 | 4.7 | 0.2 | 47.0 | 1.1 | 0.3 | 7.1 | 37.6 | 73.5 | 759.1 | | | | |
| 112.19 | 77.4 | 4.6 | 0.2 | 48.2 | 1.1 | 0.3 | 7.0 | 36.9 | 79.5 | 773.5 | 0.709 | 0.548 | 0.202 | 0.264 |

Example 7. Taxonomic Characterization of the Thraustochytrid-Like Strain G3-1

A standard approach to characterize strain G3-1 was applied. The 18S rDNA sequence was amplified from G3-1 genomic DNA using Taq DNA polymerase and primers JBo119 (5'-CAACCTGGTTGATCCTGCCAGTA-3' (SEQ ID NO:2)) and JBo120(5'-TCACTACGGAAACCTTGT-TACGAC-3' (SEQ ID NO:3)). The 50 µl PCR reaction contained 1.25 Units Taq DNA polymerase (New England Biolabs, M0273 (IpSwich, MA)), 1x standard reaction buffer, 200 µM of each dNTP (A,G,C,T), 0.2 µM of each primer (JBo119 and JBo120), and 3% DMSO. This PCR reaction was incubated at 95° C. for 4 min., then subjected to 35 cycles of 95° C. for 30 sec., 52° C. for 30 sec., and 68° C. for 1:45 min., followed by a final incubation at 68° C. for 30 min., before being held at 4° C. The ~1.7 kb amplicon was gel purified and this pool of amplified fragments was cloned into pCR2.1 vector by TA cloning to produce the plasmid pJB84. Ten individual clones of pJB84 (#1, 2, 5, 6, 7, 10, 12, 13, 14, and 15) were isolated and sent to Genewiz (South Plainfield, N.J.) for sequencing. The 18S rRNA sequence of each clone are provided in SEQ ID NOs:10, 11, 12, 13, 14, 15, 16, 17, 18, and 19. Each clone was sequenced with 8 primers in total: 4 forward primers and 4 reverse primers. Two of the sequencing primers, M13R and T7, are universal primers that bind vector sequences flanking the TA cloning site and were provided by Genewiz. The other 6 primers, including JBo119 and JBo120 used to amplify the 18S rDNA, bind within the 18S rDNA sequence and were designed based on previously reported primer sequences (Burja, A. M., Radianingtyas, H., Windust, A., and Barrow, C. J. (2006). Isolation and characterization of polyunsaturated fatty acid producing Thraustochytrium species: screening of strains and optimization of omega-3 production. Appl. Microbiol. Biotechnol. 72, 1161-1169; Mo, C., J., D., and B., R. (2002). Development of a PCR strategy for thraustochytrid identification based on 18S rDNA sequence. Mar. Biol. 140, 883-889). The 8 primer sequences are:

```
M13R
                    (SEQ ID NO: 4)
5'-CAG GAA ACA GCT ATG AC-3'
(universal primer)

T7
                    (SEQ ID NO: 5)
5'-TAA TAC GAC TCA CTA TAG GG-3'
(universal primer)

JBo119
                    (SEQ ID NO: 2)
5'-CAACCTGGTTGATCCTGCCAGTA-3'
(Burja et al. 2006)

JBo120
                    (SEQ ID NO: 3)
5'-TCACTACGGAAACCTTGTTACGAC-3'
(Burja et al. 2006)

JBo121
                    (SEQ ID NO: 6)
5'-GTCTGGTGCCAGCAGCCGCG-3'
(Mo et al. 2002)

JBo122
                    (SEQ ID NO: 7)
5'-CTTAAAGGAATTGACGGAAG-3'
(Mo etal. 2002)

JBo123
                    (SEQ ID NO: 8)
5'-AGCTTTTTAACTGCAACAAC-3'
(Mo etal. 2002)

JBo124
                    (SEQ ID NO: 9)
5'-GGCCATGCACCACCACCC-3'
(Mo etal. 2002)
```

The 8 sequencing reactions for each clone were trimmed by deleting the 5' and 3' sequences containing N's (ambiguous nucleotides) leaving only the successful portions of each sequencing read. These were assembled into a single contig for each clone using ChromasPro software (Technelysium Pty Ltd, South Brisbane, Australia). These contigs contained the 18S rDNA sequences as well as flanking vector sequences. The vector sequences were trimmed from the contig leaving only the 18S rDNA sequence amplified by JBo119 and JBo120. Any ambiguous nucleotides indicated by ChromasPro were manually determined, but there were very few, if any of these. In all cases the 18S rDNA sequence was covered by at least 2 sequencing reads over its entire length, but had at least 3 reads coverage for the vast majority of its length, with >3 reads covering some shorter spans. All 10 sequences were at least 98% identical to each other. The largest variability between any pair of clones is between #5 and #6 which are 98.19% identical. There are two pairs of clones that are 100% identical, #1 and 7, and #12 and 13, and these identical pairs are 98.98% identical to each other. A consensus sequence was created. G3-118S rDNA consensus sequence based on 10 individually sequenced clones is shown below. Degenerate nucleotides were manually curated using the standard IUPAC annotation (A, Adenine; C, Cytosine; G, Guanine; T, Thyamine; W, A or T; S, C or G; M, A or C; K, G or T; R, A or G; Y, C or T; B, not A; D, not C; H, not G; V, not T; N, any Nucleotide).

```
                                        (SEQ ID NO: 1)
CAACCTGGTTGATCCTGCCAGTAGTCATATGCTCG

TCTCAAAGATTAAGCCRTGCATGTGTAAGTATAAG

-continued
CGATTGTACTGTGAGACTGCGAACGGCTCATTATA

TCAGTAATAATTWCTTCGGTARYTTCTTTTATATG

GATACCTGCAGTAATTCTGGAAATAATACATGCTG

TAAGAGCCCTRTATGGGGCTGCACTTATTAGATTG

AAGCCGATTTTATTGGTGAATCATGATAATTGAGC

AGATTGACTWTTTTTDGTCGATGAATCGTTTGAGT

TTCTGCCCCATCAGTTGTCGACGGTAGTGTATTGG

ACTACGGTGACTATAACGGGTGACGGAGAGTTAGG

GCTCGACTCCGGAGAGGGAGCCTGAGAGACGGCTA

CCATATCCAAGGATAGCAGCAGGCGCGTAAATTAC

CCACTGTGGACTCCACGAGGTAGTGACGAGAARYA

TCGATGCGAAGCGTGTATGCGTTTTGCTATCGGAA

TGAGARYAATGTAAAACCCTCATCGAGGATCAACT

GGAGGGCAAGTCTGGTGCCAGCAGCCGCGGTRATT

CCAGCTCCRGAAGCATATGCTAAAGTTGTTGCAGT

TAAAAAGCTCGTAGTTGAATTTCTGGCATGGGCGA

CCGGTGCTTTCCCTGAATGGGGATWGATTGTCTGT

GTTGCCTTGGCCATCTTTYTCWTKYYDTTWTWGRK

RWGARATCTTTCACTGTAATCAAAGCAGAGTGTTC

CAAGCAGGTCGTATGACCGGTATGTTTATTATGGG

ATGATAAGATAGGACTTGGGTGCTATTTTGTYGGT

TTGCACGCCTGAGTAATGGTTAATAGGAACAGTTG

GGGGTATTCGTATTTAGGAGCTAGAGGTGAAATTC

TTGGATTTCCGAAAGACGAACTAGAGCGAAGGCAT

TTACMAAGCATGTTYTCATTAATCAAGAACGAAAG

TCTGGGGATCGAAGATGATTAGATACCATCGTAGT

CTAGACCGTAAACGATGCCRACTTGCGATTGTTGG

GTGCTTTWTTDTATGGGCCTCAGCAGCRGCACATG

AGARATCAAAGTCTTTGGGTTCCGGGGGAGTATG

GTCGCAAGGCTGAAACTTRAAGGAATTGACGGAAG

GGCACCACCAGGAGTGGAGCCTGCGGCTTAATTTG

ACTCAACACGGGAAAACTTACCAGGTCCAGACATA

GGTAGGATTGACAGATTGAGAGCTCTTTCATGATT

CTATGGGTGGTRGTGCATGGCCKTTCTTAGTTGGT

GGAGTGATTTGTCTGGTTAATTCCGTTAACGAACG

AGACCTCGGCCTACTAAATAGTGCGTGGTATGGCA

ACATAGTRCGTTTTWAACTTCTTAGAGGGACATGT

CCGGTTTACGGGCAGGAAGTTCGAGGCAATAACAG

GTCYGTGATGCCCTTAGATGYTCTGGGCCGCACGC

GCGCTACACTGATGGGTTCATCGGGTTTTRATTYY

AWTTWWTGGAATTGAGTGCTTGGTCGGAAGGCCTG
```

-continued

```
GCTAATCCTTGGAACGCTCATCGYGCTGGGGCTAG

ATTTTYGCAATTATTAATCTCCRACGAGGAATTCC

TAGTAAACGCAAGTCATCAGCTTGCATTGAATACG

TCCCTGCCCTTTGTACACAYCGCCCGTCGCACCTA

CCGATTGAACGGTCCGATGAAACCATGGGATGWTT

STGTTTGGATTVATTTTTSGACAKAGGCAGAACTC

GGGTGAATCTTATTGTTTAGAGGAAGGTGAAGTCG

TAACAAGGTTTCCGTAGTGA
```

Example 8. Carotenoid Characterization of the Thraustochytrid-Like Strain G3-1

Analysis of the carotenoid content of G3-1 biomass and oil was performed. Carotenoid analysis, performed on biomass from three separate 2 L fermentations, demonstrated that strain G3-1 synthesize and stores a small amount of carotenoids with β-carotene being the main components (Table 9). This contrasts with other thraustochytrids, in which canthaxanthin is the major carotenoid, but is similar to observations published for other thraustochytrid-like strains (in Lee Chang et al., "Biodiscovery of New Australian Thraustochytrids for Production of Biodiesel and Long-Chain Omega-3 Oils.").

$h^{-1}$. This alone exceed the best published TFA productivity by >80%, which is at 0.301 g $L^{-1}$ $h^{-1}$. What is more, within the produced oil DHA production is 0.202 g $L^{-1}$ $hr^{-1}$ and palmitic acid is 0.264 g $L^{-1}$ $h^{-1}$. Our analysis suggests DHA productivity compares favorably to highly optimized thraustochytrid based methods, which when cultured under conditions for the production of high DHA oil, may produce around 0.3 g $L^{-1}$ $h^{-1}$.

Example 9. Identifying Key Media Ingredients for G3-1 Biomass and Lipid Accumulation in Different Media Formulations Having Monosodium Glutamate (MSG) as the Defined Organic Nitrogen Source and Evaluation of the Fatty Acid Profile of the G3-1 Lipids Synthesized Under these Conditions Previous examples have showed that G3-1 requires a complex source of nitrogen (soy peptone and yeast extract) to grow and accumulate biomass. However, soy peptone is not only an expensive source of complex organic nitrogen, the use of high concentrations of soy peptone in the media to grow some microalgae strains have led to the synthesis of odd chain saturated fatty acids (particularly C15:0 and C17:0) in the lipid fraction of microalgae cells. For instance, G3-1 cells accumulate 15.1% of its total fatty acids as C15:0, when 20 g soy peptone $L^{-1}$ were present in the basal media that was used to grow G3-1 (Example 3). To decrease the cost of G3-1 media and to avoid having odd chain saturated

TABLE 9

Summary of carotenoid content for Thraustochytrid-like strain G3-1.
Carotenoid Concentration (per Dry weight (μg $g^{-1}$))

| Sample Day | Astaxanthin | Zeaxanthin | Canthaxanthin | β-Cryptoxanthin | Lycopene | Echinenone | β-Carotene |
|---|---|---|---|---|---|---|---|
| Replicate 1 | | | | | | | |
| 1 | 0 | 0 | 0 | 0 | 0 | 0 | 20.37 |
| 7 | 0 | 0 | 0 | 0 | 0 | 0 | 10.37 |
| 9 | 0 | 0 | 5.14 | 0 | 0 | 0 | 9.26 |
| Replicate 2 | | | | | | | |
| 1 | 0 | 0 | 0 | 0 | 0 | 0 | 23.35 |
| 7 | 0 | 0 | 0 | 0 | 0 | 0 | 6.42 |
| 9 | 0 | 0 | 0 | 0 | 0 | 0 | 7.54 |
| Replicate 3 | | | | | | | |
| 1 | 0 | 0 | 0 | 0 | 0 | 0 | 10.77 |
| 7 | 0 | 0 | 0 | 0 | 0 | 0 | 4.68 |
| 9 | 0 | 0 | 0 | 0 | 0.13 | 0 | 7.37 |

Experimental Details

For the analysis of carotenoids, biomass was extracted using small glass beads and a bead beater, in the presence of chilled acetone:methanol (1:1 v/v) twice, followed by two extractions using hexane. The combined supernatant was dried under nitrogen and re-suspended in acetone with antioxidants (0.5% butylated hydroxyanisole (BHA) and butylated hydroxytolunene (BHT). Analysis was conducted on an Agilent HPLC using a Phenomenex 5μ Luna C18(2) column.

In summary, through four experiments, which include a single media optimization and three 2 L fermentations, conditions were identified that increased biomass productivity from 0.589 g $L^{-1}$ $h^{-1}$ to 0.740 g $L^{-1}$ $h^{-1}$, and separately increase TFA synthesis from 0.396 g $L^{-1}$ $h^{-1}$ to 0.548 g $L^{-1}$ fatty acids in the lipid fraction of G3-1 cells a Plackett-Burman experimental design was used to identify key ingredients that support G3-1 cell proliferation and that must be present in a media where the use of soy peptone has been replaced by MSG and yeast extract.

Experimental Details

A Plackett-Burman design was used to identify the significance of six media ingredients on G3-1 biomass and lipid accumulation. The six media ingredients (independent variables) were tested at a high (+) and a low level (−) (Table 10). A total of twelve different media compositions for growing G3-1 having different combinations of ingredients were tested in duplicate, as described in Table 11. Based on previous experiments and in order to favor cell proliferation and lipid synthesis, for each of the twelve media compositions tested, the concentration of glucose and sodium chloride (NaCl) were kept at 40 g $L^{-1}$ and 2, respectively.

95 mL of each media tested were made following the combination of ingredients showed in Table 11 and were inoculated with 5 mL aliquots of a G3-1 seed flask. The composition of the media used for the seed flask was 20 g glucose $L^{-1}$, 30 g yeast extract $L^{-1}$ and 9 g sea salts $L^{-1}$.

TABLE 10

Independent variables and their levels used in the Plackett-Burman design.

| | | Coded level | |
|---|---|---|---|
| Variables | Code Xi | −1 | +1 |
| MSG (g $L^{-1}$) | X1 | 0 | 1 |
| Yeast extract (g $L^{-1}$) | X2 | 0 | 1 |
| KH$_2$PO$_4$ (g $L^{-1}$) | X3 | 0.1 | 0.3 |
| Trace element solution (mL$^{-1}$) | X4 | 0 | 1.5 |
| FeCl$_3$ (g $L^{-1}$) | X5 | 0 | 5 |
| MgSO$_4$•7H$_2$O (g $L^{-1}$) | X6 | 0 | 4 |

TABLE 11

Plackett-Burman design matrix.

| | | Coded Variable | | | | | | Process variable | | | | | |
|---|---|---|---|---|---|---|---|---|---|---|---|---|---|
| Run | Block | X1 | X2 | X3 | X4 | X5 | X6 | X1 | X2 | X3 | X4 | X5 | X6 |
| 1 | 1 | +1 | −1 | +1 | −1 | −1 | −1 | 1 | 0 | 0.3 | 0 | 0 | 0 |
| 2 | 1 | +1 | +1 | −1 | +1 | −1 | −1 | 1 | 1 | 0.1 | 1.5 | 0 | 0 |
| 3 | 1 | −1 | +1 | +1 | −1 | +1 | −1 | 0 | 1 | 0.3 | 0 | 5 | 0 |
| 4 | 1 | +1 | −1 | +1 | +1 | −1 | +1 | 1 | 0 | 0.3 | 1.5 | 0 | 4 |
| 5 | 1 | +1 | +1 | −1 | +1 | +1 | −1 | 1 | 1 | 0.1 | 1.5 | 5 | 0 |
| 6 | 1 | +1 | +1 | +1 | −1 | +1 | +1 | 1 | 1 | 0.3 | 0 | 5 | 4 |
| 7 | 1 | −1 | +1 | +1 | +1 | −1 | +1 | 0 | 1 | 0.3 | 1.5 | 0 | 4 |
| 8 | 1 | −1 | −1 | +1 | +1 | +1 | −1 | 0 | 0 | 0.3 | 1.5 | 5 | 0 |
| 9 | 1 | −1 | −1 | −1 | +1 | +1 | +1 | 0 | 0 | 0.1 | 1.5 | 5 | 4 |
| 10 | 1 | +1 | −1 | −1 | −1 | +1 | +1 | 1 | 0 | 0.1 | 0 | 5 | 4 |
| 11 | 1 | −1 | +1 | −1 | −1 | −1 | +1 | 0 | 1 | 0.1 | 0 | 0 | 4 |
| 12 | 1 | −1 | −1 | −1 | −1 | −1 | −1 | 0 | 0 | 0.1 | 0 | 0 | 0 |

In addition to glucose (40 g $L^{-1}$), sodium chloride (2 g $L^{-1}$), yeast extract and MSG, the most significant ingredients (p<0.05) that must be added to the media to favor G3-1 cell proliferation were: MgSO$_4$·7H$_2$O (×6), trace elements (×4) and KH$_2$PO$_4$ (×3). The highest biomass accumulation (13·2±0.1 g $L^{-1}$) was obtained using a media having at least 1 g yeast extract $L^{-1}$, 1 g MSG $L^{-1}$, 0.3 g KH$_2$PO$_4$ $L^{-1}$, 1.5 mL $L^{-1}$, 4 g MgSO$_4$·7H$_2$O $L^{-1}$, 40 g glucose $L^{-1}$ and 2 g NaCl $L^{-1}$. FeCl$_3$ did not show a significant effect (p>0.05) on G3-1 biomass accumulation, so it was eliminated from the media formulation to grow G3-1.

Figure 8:
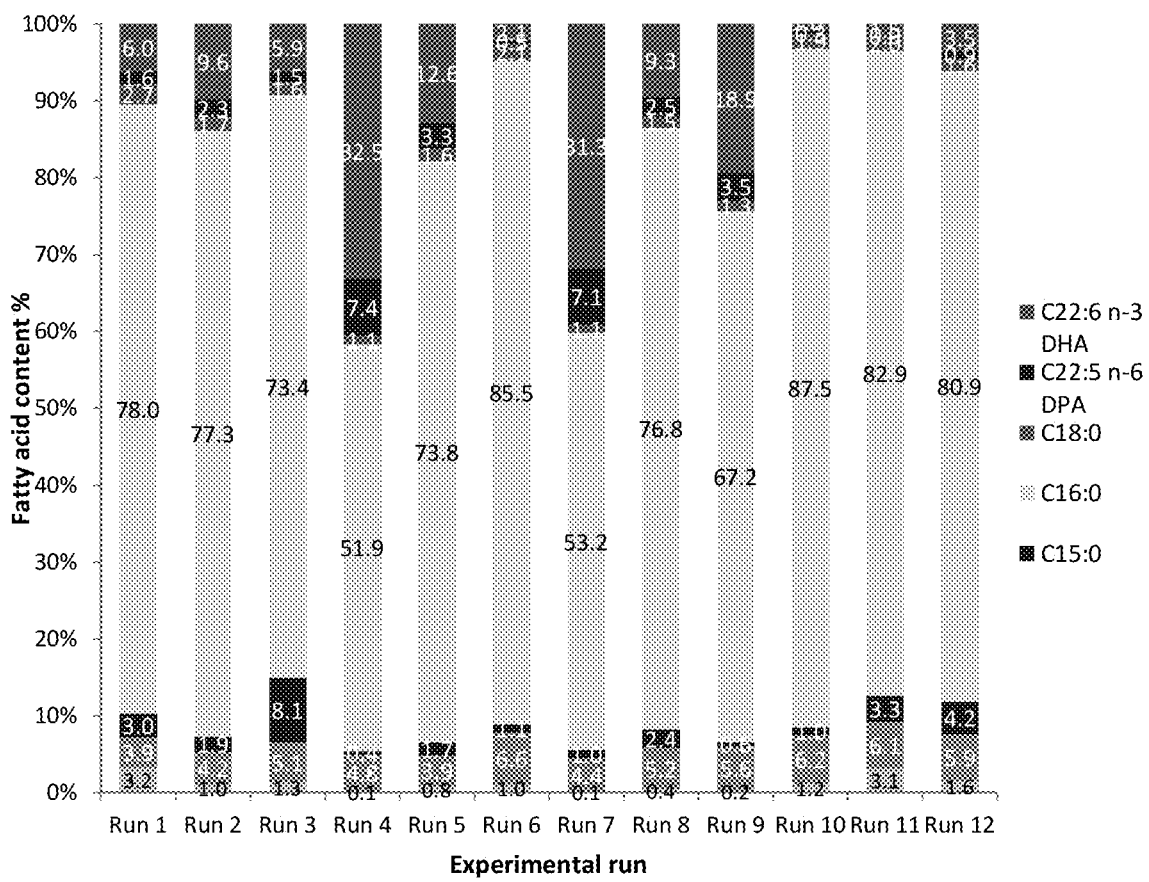
FIG. 8 is a graph showing the fatty acid profile of the intracellular oil of strain G3-1 under different liquid media compositions.

On the other hand, ANOVA of the lipid accumulation data for each of the medias tested by using the Plackett-Burman design showed that MgSO$_4$·7H$_2$O (×6), trace elements (×4) and KH$_2$PO$_4$ (×3) had a positive significant effect (p<0.05) on lipid accumulation expressed as total fatty acids (TFA). MSG also had a statistically significant effect on TFA concentration, however its effect on TFA was negative, which means that G3-1 synthesized less lipids when the concentration of MSG in the media was high. This was expected, because low carbon to nitrogen ratios (C/N) affect lipid biosynthesis in G3-1 cells. The best combination of media ingredients to obtain the highest TFA (789 mg $g^{-1}$) were: at least 1 g yeast extract $L^{-1}$, 0.3 g KH$_2$PO$_4$ $L^{-1}$, 1.5 mL trace elements $L^{-1}$, 4 g MgSO$_4$·7H$_2$O $L^{-1}$, 40 g glucose $L^{-1}$ and 2 g NaCl $L^{-1}$. In addition to affecting biomass and TFA production, fatty acid profile was also influenced by the different media compositions tested by using the Plackett-Burman design (FIG. 8). For instance, media formulations for run 10, 11 and 12 of the Plackett-Burman design matrix (Table 12) showed a very low DHA content: 1, 1.5 and 3.5, respectively; whereas C16:0 content (%) was 87.5, 82.9 and 80.9, respectively. The media for runs 10, 11 and 12 lack trace elements solution, this ingredient is not only required for G3-1 cell proliferation but it also has to be added to the media to enhance lipid biosynthesis and to favor accumulation of lipids with a more balanced fatty acid profile, such as the oily biomass obtained for run 4 and 7 (Table 12, FIG. 8).

TABLE 12

Fatty acid profile of the intracellular oil of strain G3-1 under different liquid media compositions tested using a Plackett-Burman design.

| | Fatty acids (%) | | | | | | | | | | | |
|---|---|---|---|---|---|---|---|---|---|---|---|---|
| Run | C10:0 | C14:0 | C15:0 | C16:0 | C18:0 | C22:5 n-6 DPA | C22:6 n-3 DHA | SFA | MUFA | PUFA | Biomass (g/L) | TFA (g/L d) |
| 1 | 3.2 | 3.9 | 3.0 | 78.0 | 2.7 | 1.6 | 6.0 | 92.3 | 0 | 7.7 | 0.5 ± 0.02 | 0.04 |
| 2 | 1.0 | 4.2 | 1.9 | 77.3 | 1.7 | 2.3 | 9.6 | 87.3 | 0.2 | 12.5 | 3.5 ± 0.2 | 0.5 |
| 3 | 1.3 | 5.1 | 8.1 | 73.4 | 1.6 | 1.5 | 5.9 | 92.5 | 0 | 7.5 | 1.3 ± 0.05 | 0.2 |
| 4 | 0.1 | 4.8 | 0.4 | 51.9 | 1.1 | 7.4 | 32.5 | 58.9 | 0.2 | 41.0 | 13.2 ± 0.1 | 3.5 |
| 5 | 0.8 | 3.9 | 1.7 | 73.8 | 1. | 3.3 | 12.6 | 83.2 | 0.3 | 16.5 | 3.5 ± 0.1 | 0.4 |
| 6 | 1.0 | 6.6 | 1.1 | 85.5 | 2.1 | 0.5 | 2.1 | 97.5 | 0 | 2.5 | 5.8 ± 0.01 | 0.9 |

TABLE 12-continued

Fatty acid profile of the intracellular oil of strain G3-1 under different liquid media compositions tested using a Plackett-Burman design.

| | Fatty acids (%) | | | | | | | | | | | |
|---|---|---|---|---|---|---|---|---|---|---|---|---|
| Run | C10:0 | C14:0 | C15:0 | C16:0 | C18:0 | C22:5 n-6 DPA | C22:6 n-3 DHA | SFA | MUFA | PUFA | Biomass (g/L) | TFA (g/L d) |
| 7 | 0.1 | 4.4 | 1.0 | 53.2 | 1.1 | 7.1 | 31.3 | 60.4 | 0.1 | 39.5 | 9.4 ± 0.1 | 2.6 |
| 8 | 0.4 | 5.2 | 2.4 | 76.8 | 1.5 | 2.5 | 9.3 | 87.6 | 0.1 | 12.2 | 3.3 ± 0.1 | 0.6 |
| 9 | 0.2 | 5.6 | 0.6 | 67.2 | 1.3 | 3.5 | 18.9 | 75.5 | 0.1 | 24.3 | 6.2 ± 0.2 | 1.4 |
| 10 | 1.2 | 6.2 | 1.0 | 87.5 | 1.9 | 0.3 | 1.0 | 98.6 | 0.2 | 1.3 | 5.9 ± 0.2 | 0.9 |
| 11 | 3.1 | 6.1 | 3.3 | 82.9 | 2.0 | ND | 1.5 | 98.5 | 0 | 1.5 | 3.1 ± 0.2 | 0.5 |
| 12 | 1.6 | 5.9 | 4.2 | 80.9 | 1.6 | 0.9 | 3.5 | 95.6 | 0 | 4.4 | 2.5 ± 0.04 | 0.4 |

ND not detectable

Example 10. The Effect of a Complex Nitrogen Source (Yeast Extract), a Simple Organic Nitrogen Source (MSG) and a Simple Inorganic Nitrogen Source (Ammonium Sulfate, $(NH_4)_2SO_4$) on G3-1 Biomass Accumulation G3-1 cells showed the ability to accumulate biomass in a liquid media lacking soy peptone but having MSG and yeast extract as the simple and complex organic nitrogen sources, respectively. Previous examples described in this document have demonstrated that G3-1 requires high concentrations of complex and simple organic nitrogen in order to accumulate a decent amount of biomass. Formulation of media and development of fermentation strategies to produce high concentrations of oily G3-1 biomass are imperative when developing microalgae fermentation technologies to produce value-added products, such as DHA, protein, carotenoids, etc.

Experimental Details

In this example, the effect of three different nitrogen sources (yeast extract, MSG and $(NH_4)_2SO_4$) on biomass accumulation by G3-1 were tested by using a two-level full factorial design ($2^3$). The concentration of the three nitrogen sources (independent variables) were tested at a high (+) and a low level (−) (Table 13). A total of eight different media compositions for growing G3-1 having different combinations of yeast extract, MSG and $(NH_4)_2SO_4$ were tested in duplicate, as described in Table 14. Based on previous examples and in order to favor cell proliferation, for each of the eight media compositions tested, the concentration of glucose, NaCl, $MgSO_4 \cdot 7H_2O$, trace elements solution, $KH_2PO_4$, $K_2HPO_4$, $CaCl_2$) and vitamin B solution were kept at 40 g $L^{-1}$, 2 g $L^{-1}$, 4 g $L^{-1}$, 1.5 mL $L^{-1}$, 1.6 g $L^{-1}$, 1.74 g $L^{-1}$, 0.5 mL $L^{-1}$ and 1 mL $L^{-1}$, respectively. 95 mL of each media tested were made following the combination of ingredients showed in Table 14 and were inoculated with 5 mL aliquots of pure washed G3-1 cultures.

TABLE 13

Independent variables and their levels used in the full factorial design ($2^3$).

| | | Coded level | |
|---|---|---|---|
| Variables | Code Xi | −1 | +1 |
| Yeast extract (g $L^{-1}$) | X1 | 5 | 15 |
| MSG (g $L^{-1}$) | X2 | 1 | 20 |
| $(NH_4)_2SO_4$ (g $L^{-1}$) | X3 | 5 | 10 |

TABLE 14

Full factorial $2^3$ design matrix and biomass results.

| | | Coded Variable | | | Process variable | | | Biomass |
|---|---|---|---|---|---|---|---|---|
| Run | Block | X1 | X2 | X3 | X1 | X2 | X3 | (g/L) |
| 1 | 1 | −1 | −1 | −1 | 5 | 1 | 5 | 11.5 ± 0.2 |
| 2 | 1 | +1 | −1 | −1 | 15 | 1 | 5 | 18.5 ± 0.2 |
| 3 | 1 | −1 | +1 | −1 | 5 | 20 | 5 | 29.5 ± 0.6 |
| 4 | 1 | +1 | +1 | −1 | 15 | 20 | 5 | 32.5 ± 0.2 |
| 5 | 1 | −1 | −1 | +1 | 5 | 1 | 10 | 10.5 ± 1.0 |
| 6 | 1 | +1 | −1 | +1 | 15 | 1 | 10 | 19.0 ± 0.3 |
| 7 | 1 | −1 | +1 | +1 | 5 | 20 | 10 | 29.8 ± 0.3 |
| 8 | 1 | +1 | +1 | +1 | 15 | 20 | 10 | 30.7 ± 0.4 |

The ANOVA of the biomass data showed that the most statistically significant ($p<0.05$) nitrogen sources influencing biomass accumulation were: MSG and yeast extract. The interaction between MSG and yeast extract was also significant ($p<0.05$), which means that, G3-1 cells prefers to uptake MSG first and then start to use yeast extract as the nitrogen source. The highest biomass concentration for this example (32.5±0.5 g $L^{-1}$) was obtained when G3-1 was grown in a media having 15 g yeast extract $L^{-1}$, 20 g MSG $L^{-1}$ and 5 g $(NH_4)_2SO_4$ $L^{-1}$ (run 4 Table 14). Run 8 also showed a good accumulation of biomass (30.7±0.4 g $L^{-1}$), however this media formulation requires 50% more $(NH_4)_2SO_4$ compared to run 4.

Based on the results described on this example, media formulations for run 4 and 8 were named VU1 and VU2, respectively, and were selected to develop fermentation processes to obtain two different G3-1 biomass products: (1)

oily biomass having at least 60% lipids and 35% C22:6n-3 (DHA) in the triglycerides in the total fatty acids, and (2) biomass having at least 18% true protein in the whole algae biomass. True protein is expressed as the sum of amino acid concentrations in the biomass sample.

Example 11. Production of Omega-3 Rich Oily Biomass

VU1 media formulation was selected to carry out a fermentation using a 30 L fermenter to obtain omega-3 rich oily biomass with applications in aquafeed. In this 116.5 h fermentation G3-1 produced 98.4 g $L^{-1}$ biomass composed of 66.2% TFA and 8% true protein. DHA and palmitic acid constituted 39.4% and 46.1% of TFA, respectively.

Experimental Details

Figure 9:
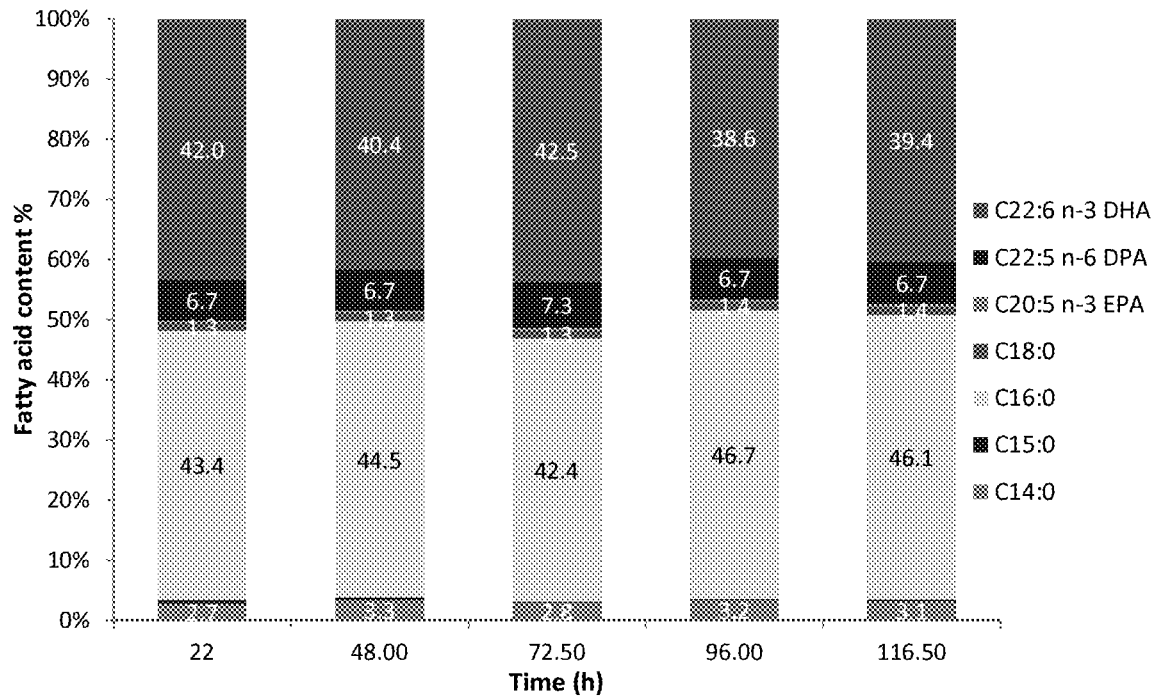
FIG. 9 is a graph showing the fatty acid profile of the intracellular oil of strain G3-1. Cells were cultured in 30 L fermenter using VU1 media.

G3-1 was pre-cultured in Erlenmeyer flasks containing 500 mL of seed flask media (20 g glucose $L^{-1}$, 5 g yeast extract $L^{-1}$, 2 g NaCl $L^{-1}$, 4 g $MgSO_4$ $L^{-1}$, 3 mg copper sulfate $L^{-1}$, 2 mg sodium molybdate $L^{-1}$, 3 mg zinc sulfate $L^{-1}$, 2 mg cobalt (II) chloride $L^{-1}$, 2 mg manganese chloride $L^{-1}$ and 2 mg nickel sulfate $L^{-1}$). Flasks were incubated under agitation at 25° C. and 200 rpm for 2 days. After the incubation period, 1 L of the pre-cultured cells were transferred into a 19 L of VU1 media. The composition of VU1 media per liter was: 15 g yeast extract, 20 g MSG, 5 g $(NH_4)_2SO_4$, 40 g glucose, 2 g NaCl, 4 g $MgSO_4$, 1.6 g $KH_2PO_4$, 1.75 g $K_2HPO_4$, 3 mg copper sulfate, 2 mg sodium molybdate, 3 mg zinc sulfate, 2 mg cobalt (II) chloride, 2 mg manganese chloride, 2 mg nickel sulfate, 0.1 g calcium chloride dehydrate, 0.01 g cobalamin, 0.01 g biotin and 2 g thiamin hydrochloride. A batch fermentation was carried out in a 30 L fermenter under the following conditions: 25° C., pH 6.8, aeration at 0.5 VVM with atmospheric air, agitation starting at 357 rpm and reaching 447 rpm. Cells were collected at 10-18 h intervals and the biomass, TFA, DHA and protein were measured. The initial glucose in the media was completely depleted after 24 h of fermentation and at that time the culture was then fed with 75% (w/v) glucose, until 116.5 h when the fermentation was ended. For this fermentation productivity for biomass, TFA and DHA was: 0.84 g $L^{-1}$ $h^{-1}$, 0.56 g $L^{-1}$ $h^{-1}$ and 0.22 g $L^{-1}$ $h^{-1}$, respectively (Table 15, FIG. 9). On the other hand, biomass at the end of the fermentation had 8% true protein.

The fermentation technology developed to produce G3-1 omega-3 rich oily biomass can easily achieve ≥15 g/L d productivity in biomass, 66% lipid and >39% DHA in 4.9 days. A biomass with this composition could be used to feed fish in in vivo trials to assess its suitability as a DHA rich aquafeed product for farmed fish.

Example 12. Production of Omega-3 Rich Microalgae Biomass with a Higher Protein Content VU2 media formulation was selected to carry out a fermentation using a 30 L fermenter to obtain omega-3 rich biomass high in protein. A biomass product having high DHA and high protein while still containing 30-45% lipids has the potential to be used as an aquafeed product. In this 72 h fermentation G3-1 produced 93.4 g $L^{-1}$ biomass composed of 43.6% TFA, 47.8% DHA, 36.9% palmitic acid and 18.6% true protein.

Experimental Details

G3-1 was pre-cultured in Erlenmeyer flasks containing 500 mL of seed flask media (20 g glucose $L^{-1}$, 5 g yeast extract $L^{-1}$, 2 g NaCl $L^{-1}$, 4 g $MgSO_4$ $L^{-1}$, 3 mg copper sulfate $L^{-1}$, 2 mg sodium molybdate $L^{-1}$, 3 mg zinc sulfate $L^{-1}$, 2 mg cobalt (II) chloride $L^{-1}$, 2 mg manganese chloride $L^{-1}$ and 2 mg nickel sulfate $L^{-1}$). Flasks were incubated under agitation at 25° C. and 200 rpm for 2 days. After the incubation period, 1 L of the pre-cultured cells were transferred into a 19 L of VU2 media. The composition of VU2 media per liter was: 15 g yeast extract, 20 g MSG, 10 g $(NH_4)_2SO_4$, 40 g glucose, 2 g NaCl, 4 g $MgSO_4$, 1.6 g $KH_2PO_4$, 1.75 g $K_2HPO_4$, 3 mg copper sulfate, 2 mg sodium molybdate, 3 mg zinc sulfate, 2 mg cobalt (II) chloride, 2 mg manganese chloride, 2 mg nickel sulfate, 0.1 g calcium chloride dehydrate, 0.01 g cobalamin, 0.01 g biotin and 2 g thiamin hydrochloride. A batch fermentation was carried out in a 30 L fermenter under the following conditions: 25° C., aeration at 0.5 VVM with atmospheric air, agitation starting at 357 rpm and reaching 370 rpm. Finally, the pH of the culture was kept around 6.2 by using an aqueous solution of ammonium hydroxide. Cells were collected at 6-18 h intervals and the biomass, TFA, DHA and protein were measured. The initial glucose in the media was completely depleted after 22 h of fermentation and at that time the culture was then fed with 75% (w/v) glucose, until 72 h

TABLE 15

Oil production and fatty acid profile of the intracellular oil of MARA G3-1. Cells were cultured in a 30 L fermenter using VU1 media.

Figure 10:
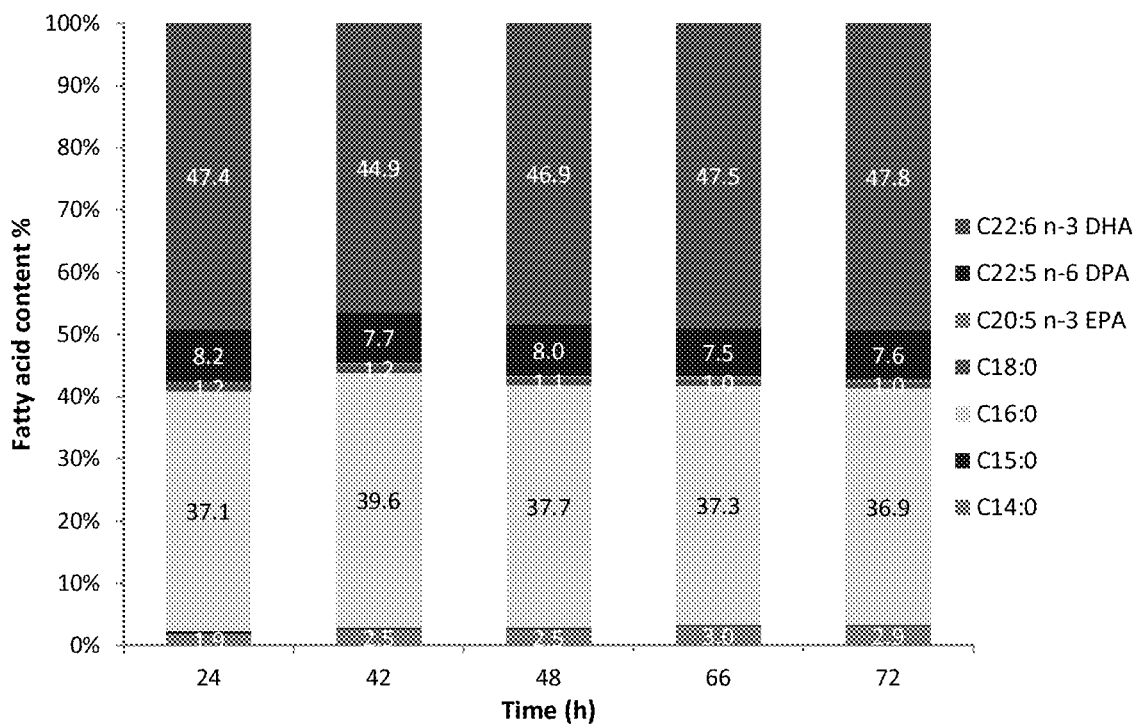
FIG. 10 is a graph showing the fatty acid profile of the intracellular oil of strain G3-1. Cells were cultured in 30 L fermenter using VU2 media.

| | | | | | | Fatty acids (%) | | | | | | | | |
|---|---|---|---|---|---|---|---|---|---|---|---|---|---|---|
| | | | | | | | C20:5 | C22:5 | C22:6 | | | | | |
| Time | TFA | | | | | | (n-3) | (n-6) | (n-3) | Biomass | TFA | | Productivity (g/L h) | |
| (h) | (%) | C14:0 | C15:0 | C16:0 | C18:0 | | EPA | DPA | DHA | (g/L) | (mg/g) | Biomass | TFA | DHA | C16:0 |
| 22 | 27 | 2.7 | 0.6 | 43.4 | 1.3 | | 0.3 | 6.7 | 42 | 26 | 269.5 | | | | |
| 48 | 44.1 | 3.3 | 0.4 | 44.5 | 1.3 | | 0.4 | 6.7 | 40.4 | 57 | 441.3 | | | | |
| 72.5 | 57.7 | 2.8 | 0.2 | 42.4 | 1.3 | | 0.4 | 7.3 | 42.5 | 87.4 | 577.3 | | | | |
| 96 | 60.6 | 3.2 | 0.2 | 46.7 | 1.4 | | 0.4 | 6.7 | 38.6 | 96.8 | 605.9 | | | | |
| 116.5 | 66.2 | 3.1 | 0.2 | 46.1 | 1.4 | | 0.5 | 6.7 | 39.4 | 98.4 | 662.2 | 0.84 | 0.56 | 0.22 | 0.26 | when the fermentation was ended. For this fermentation productivity for biomass, TFA and DHA was: 1.3 g $L^{-1}$ $h^{-1}$, 0.57 g $L^{-1}$ $h^{-1}$ and 0.27 g $L^{-1}$ $h^{-1}$, respectively (Table 16, FIG. 10).

VU3 to grow G3-1 under heterotrophic conditions. In this 118.5 h fermentation G3-1 produced 61.7 g $L^{-1}$ biomass composed of 15.6% TFA, 55% DHA, 19.7% palmitic acid and 4.1% EPA.

TABLE 16

Oil production and fatty acid profile of the intracellular oil of MARA G3-1. Cells were cultured in a 30 L fermenter using VU2 media.

| Time (h) | TFA (%) | Fatty acids (%) | | | | | | | Biomass (g/L) | TFA (mg/g) | Productivity (g/L h) | | | | True protein (%) |
|---|---|---|---|---|---|---|---|---|---|---|---|---|---|---|---|
| | | C14:0 | C15:0 | C16:0 | C18:0 | C20:5 (n-3) EPA | C22:5 (n-6) DPA | C22:6 (n-3) DHA | | | Biomass | TFA | DHA | C16:0 | |
| 24 | 17   | 1.9 | 0.4 | 37.1 | 1.2 | 0.3 | 8.2 | 47.4 | 27.8 | 170.4 |     |      |      |      |      |
| 42 | 25.8 | 2.5 | 0.3 | 39.6 | 1.2 | 0.4 | 7.7 | 44.9 | 54.2 | 257.8 |     |      |      |      |      |
| 48 | 30.2 | 2.5 | 0.2 | 37.7 | 1.1 | 0.4 | 8.0 | 46.9 | 62.4 | 302.2 |     |      |      |      |      |
| 66 | 42.7 | 3.0 | 0.2 | 37.3 | 1.0 | 0.4 | 7.5 | 47.5 | 86.0 | 426.6 |     |      |      |      |      |
| 72 | 43.6 | 2.9 | 0.2 | 36.9 | 1.0 | 0.4 | 7.6 | 47.8 | 93.4 | 435.6 | 1.3 | 0.57 | 0.27 | 0.21 | 18.6 |

The fermentation process described in this example produced a G3-1 biomass product not only rich in omega-3 DHA but also with a higher protein content compared to the product described as omega-3 rich oily G3-1 biomass. Growing G3-1 in VU2 media and using an aqueous solution of ammonium hydroxide to control the pH and also to pulse nitrogen into the vessel not only modified the C/N ratio in the fermentation broth but also, favored nitrogen metabolic pathways in the cells which in turn limited the ability of G3-1 to synthesized lipids, improving G3-1 protein content. 31.1 g/L d productivity in biomass, 43.6% lipid, >47% DHA and 18.6% true protein can easily be achieved in 3 days by following the fermentation technology described in this example.

Figure 11:
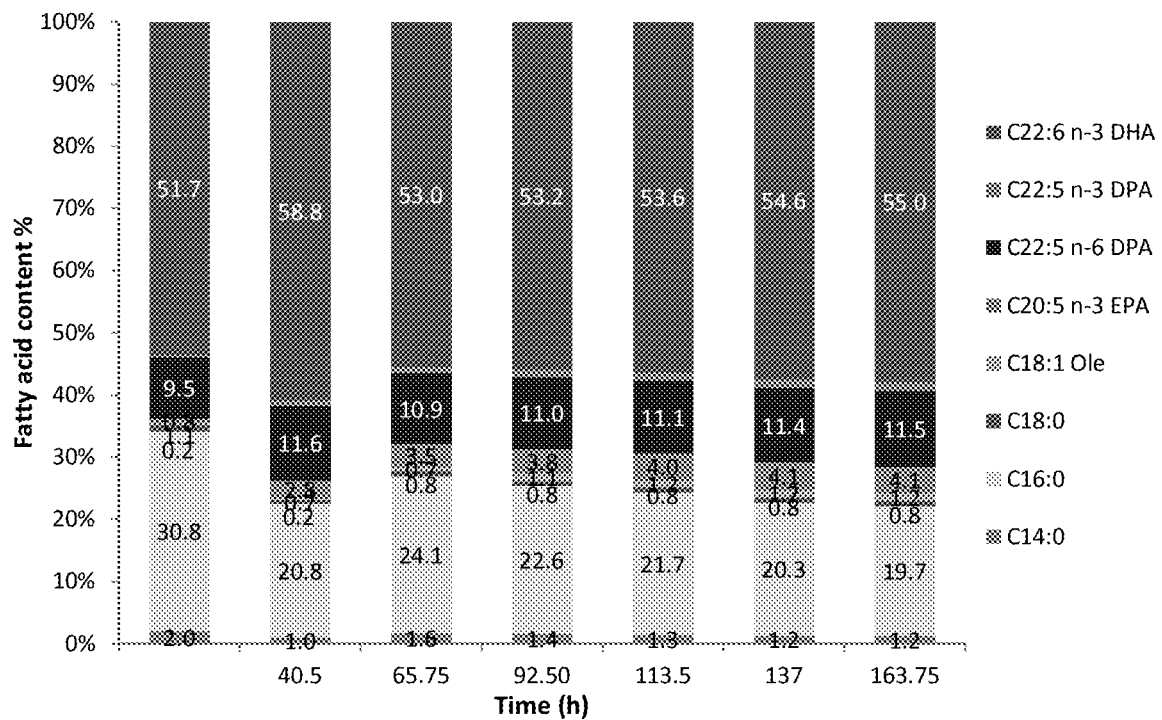
FIG. 11 is a graph showing the fatty acid profile of the intracellular oil of strain G3-1. Cells were cultured in 2 L fermenter using VU3 media and crude glycerol as the carbon source.

Example 13. Production of G3-1 Biomass Low in Lipids and Enhancement of DHA and EPA (Expressed as Percentage of Total Fatty Acids) by Using Crude Glycerol from Biodiesel Production The potential use of crude glycerol to cultivate oleaginous microorganisms has grown in popularity, essentially to reduce cultivation costs. Simultaneously, the need to valorize glycerol as a co-product of biodiesel has arisen as a result of the biofuel boom. Depending on the feedstock and the process used to produce biodiesel, the contaminants present in crude glycerol vary. The most common ones are methanol and soap, but also high salinity. As a consequence, tons of raw glycerol need to be valorized or classified as industrial waste. The high salinity of crude glycerol has undesired effects on many organism, however, it favors the use of marine microalgae. Fermentation processes based on crude glycerol as the carbon source aiming to obtain higher quantities of value-added metabolites, such as PUFAs, particularly EPA and DHA are the ones with the highest value (Abad and Turon, Mar. Drugs. 13:7275 (2015)). Previous efforts to use crude glycerol in marine microalgae fermentation bioprocesses have focused on the production of high concentrations of intracellular lipids, however, there is little information regarding the use of a fermentation process to delay oil accumulation in oleaginous microorganisms while using crude glycerol as the carbon source. In this example, a crude glycerol feedstock having 1120 g glycerol $L^{-1}$ was used in combination with a liquid media formulation called Experimental Details G3-1 was pre-cultured in Erlenmeyer flasks containing 250 mL of seed flask media (20 g glucose $L^{-1}$, 5 g yeast extract $L^{-1}$, 2 g NaCl $L^{-1}$, 4 g MgSO$_4$ $L^{-1}$, 1 g MSG $L^{-1}$, and 3 mg copper sulfate $L^{-1}$, 2 mg sodium molybdate $L^{-1}$, 3 mg zinc sulfate $L^{-1}$, 2 mg cobalt (II) chloride $L^{-1}$, 2 mg manganese chloride $L^{-1}$ and 2 mg nickel sulfate $L^{-1}$). Flasks were incubated under agitation at 25° C. and 200 rpm for 2 days. After the incubation period, 0.14 L of the pre-cultured cells were transferred into 1.26 L of VU3 media. The composition of VU3 media per liter was: 2 g yeast extract, 5 g MSG, 10 g (NH$_4$)$_2$SO$_4$, 66 g crude glycerol, 2 g NaCl, 4 g MgSO$_4$, 1.6 g KH$_2$PO$_4$, 1.75 g K$_2$HPO$_4$, 3 mg copper sulfate, 2 mg sodium molybdate, 3 mg zinc sulfate, 2 mg cobalt (II) chloride, 2 mg manganese chloride, 2 mg nickel sulfate, 0.1 g calcium chloride dehydrate, 0.01 g cobalamin, 0.01 g biotin and 2 g thiamin hydrochloride. A batch fermentation was carried out in a 2 L fermenter under the following conditions: 25° C., aeration at 1 VVM with atmospheric air, agitation starting at 550 rpm and reaching 710 rpm. During the first 65.75 h of fermentation the pH of the culture was kept around 6.16-6.26 by using an aqueous solution of ammonium hydroxide. Then the ammonium hydroxide solution was swapped by 5 M NaOH to keep the pH around 6.05 up to 188.5 h of fermentation. Cells were collected at 6-18 h intervals and the biomass, TFA, palmitic acid, DHA and EPA were measured. The initial glucose in the media was completely depleted after 40 h of fermentation and at that time the culture was then fed with 1120 g crude glycerol $L^{-1}$, until 188.5 h when the fermentation was stopped. At the end of the process productivity for biomass and TFA was 0.33 g $L^{-1}$ $h^{-1}$ and 0.05 g $L^{-1}$ $h^{-1}$. On the other hand, DHA and EPA content (expressed as % of TFA) was 55% and 4.1%. In previous examples G3-1 has shown a poor ability to accumulate EPA in its lipid fraction with contents ranging from 0.5 to 1% of TFA when glucose was used as the carbon source, however under the conditions described in this example, the amount of EPA synthesized by G3-1 was 3 times higher (Table 17, FIG. 11). Adverse culture conditions such as nutrient deficiency or toxic compounds in the liquid media stimulated the synthesis of EPA by thraustochytrids. It is hypothesized that the biosynthesis of EPA and other PUFAs by thraustochytrids is to provide antioxidant power to protect the cells when subjected to oxidative stress (Ugalde et al., J. Appl. Phycol. (2017)).

TABLE 17

Oil production and fatty acid profile of the intracellular oil of MARA G3-1. Cells were cultured in a 2 L fermenter using VU3 media and crude glycerol as the carbon source.

| Time (h) | TFA (%) | C14:0 | C16:0 | C18:0 | C18:1 oleic | C20:5 (n-3) EPA | C22:5 (n-6) DPA | C22:5 (n-3) DPA | C22:6 (n-3) DHA | Biomass (g/L) | TFA (mg/g) | Productivity (g/L h) Biomass | TFA | DHA | C16:0 |
|---|---|---|---|---|---|---|---|---|---|---|---|---|---|---|---|
| 40.5 | 17.9 | 2.0 | 30.8 | 1.1 | 0.2 | 0.8 | 9.5 | 0.3 | 51.7 | 36.9 | 178.7 | | | | |
| 65.75 | 12.4 | 1.0 | 20.8 | 0.7 | 0.2 | 2.8 | 11.6 | 0.8 | 58.8 | 27.8 | 124.2 | | | | |
| 92.50 | 13.3 | 1.6 | 24.1 | 0.8 | 0.7 | 3.5 | 10.9 | 1.0 | 53.0 | 47.6 | 132.7 | | | | |
| 113.5 | 14.4 | 1.4 | 22.6 | 0.8 | 1.1 | 3.8 | 11.0 | 1.1 | 53.2 | 53.9 | 143.5 | | | | |
| 137 | 15.1 | 1.3 | 21.7 | 0.8 | 1.2 | 4.0 | 11.1 | 1.2 | 53.6 | 57.4 | 151.0 | | | | |
| 163.75 | 15.1 | 1.2 | 20.3 | 0.8 | 1.2 | 4.1 | 11.4 | 1.3 | 54.6 | 59.8 | 151.3 | | | | |
| 188.5 | 15.6 | 1.2 | 19.7 | 0.8 | 1.2 | 4.1 | 11.5 | 1.4 | 55.0 | 61.7 | 155.9 | 0.33 | 0.05 | 0.03 | 0.01 |

74.5 mL of an ammonium hydroxide solution were pulsed into the 2 L vessel during the first 65.75 h of fermentation. From 65.75 h to 188.5 h the ammonium hydroxide solution was swapped for a solution of NaOH 5 M to keep pH around 6.05 and push G3-1 cells to accumulate lipids. As seen on Table 17 pulsing nitrogen in the form of ammonium hydroxide helped to increase the biomass content, however, swapping ammonium hydroxide solution for NaOH 5M and keeping the fermentation running for an extra five days did not favor lipid accumulation in G3-1 cells. G3-1 cells uptake nitrogen in the form of ammonium hydroxide but it seems that catabolism of ammonium hydroxide interferes with the lipid biosynthesis pathways in G3-1. On the other hand, not only ammonium sulfate but the crude glycerol used as a carbon feedstock could have stressed G3-1 cells. The crude glycerol used in the present example, contains 0.8% methanol and a high salinity, these impurities act as stress factors even for marine microalgae that can tolerate high salinity environments. It has been reported that abiotic stress often causes amino acids, which serve as potential stress mitigators, to accumulate. In addition to being the building blocks of proteins, amino acids serve as the precursors of N-containing molecules such as nucleic acids, polyamines, quaternary ammonium compounds, and some hormones. Under environmental stress, de novo protein synthesis is generally inhibited and protein turnover and proteolytic activity are increased, resulting in an increase of total free amino acids. N and C metabolisms are closely connected; N assimilation and amino acid biosynthesis require reducing equivalents from carbon metabolism (e.g., glucose, glycerol, etc.) and C skeletons from the tricarboxylic acid (TCA) cycle (Chen et al., Biotechnol. Biofuels 10:153 (2017)). At the end of the fermentation (e.g., at 188.5 h) G3-1 cells accumulated 15.6% of intracellular lipids (Table 17) even though G3-1 cells consumed 160.5 g of crude glycerol. It seems that the energy and C skeletons generated from the crude glycerol metabolism were not used for lipid accumulation but were redirected to different metabolic pathways in G3-1 cells.

What is claimed is:

1. A method of making a lipid composition, the method comprising
   (a) culturing a eukaryotic microorganism comprising SEQ ID NO: 1 in a heterotrophic medium to produce cultured microorganisms comprising a biomass comprising the lipid composition comprising a simple lipid profile comprising long chain fatty acids (LCFAs), wherein the simple lipid profile comprises triglycerides and wherein greater than 95% of the triglycerides are comprised of myristic acid (C14:0), palmitic acid (C16:0), docosapentaenoic acid n-6 (C22:5n-6, DPAn6), and docosahexaenoic acid (C22:6n-3, DHA), wherein the eukaryotic microorganism comprises SEQ ID NO: 1, wherein SEQ ID NO: 1 comprises an A or G at position 52, an A or T at position 118, an A or G at position 127, a C or T at position 128, an A or G at position 186, an A or T at position 255, an A, G or T at position 261, an A or G at position 453, a C or T at position 454, an A or G at position 496, a C or T at position 497, an A or G at position 557, an A or G at position 569, an A or T at position 655, a C or T at position 684, an A or T at position 687, a G or T at position 689, a C or T at position 690, a C or T at position 691, an A, G or T at position 692, an A or T at position 695, an A or T at position 697, an A or G at position 699, a G or T at position 700, an A or G at position 701, an A or T at position 702, an A or G at position 705, a C or T at position 802, an A or C at position 915, a C or T at position 925, an A or T at position 1000, an A, G or T at position 1023, an A, G or T at position 1026, an A or G at position 1043, an A or G at position 1054, an A or G at position 1104, an A or G at position 1237, a G or T at position 1248, an A or G at position 1338, an A or T at position 1345, a C or T at position 1404, a C or T at position 1421, an A or G at position 1465, a C or T at position 1469, a C or T at position 1470, an A or T at position 1472, an A or T at position 1475, an A or T at position 1476, a C or T at position 1529, a C or T at position 1546, an A or G at position 1563, a C or T at position 1630, an A or T at position 1678, a C or G at position 1681, an A, C or G at position 1692, a C or G at position 1699, and a G or T at position 1704; and
   (b) isolating the lipid composition.

2. The method of claim 1, wherein the heterotrophic medium contains less than 3.75 g/L chloride.

3. The method of claim 1, wherein the cultured microorganisms have a biomass productivity of greater than 0.65 g/L/h.

4. The method of claim 1, wherein the cultured microorganisms have a triglyceride productivity of greater than 0.3 g/L/h.

5. The method of claim 1, wherein the simple lipid profile comprises less than 3% of each of lauric acid (C12:0), pentadecylic acid (C15:0), palmitoleic acid (C16:1), margaric acid (C17:0), stearic acid (C18:0), vaccenic acid (C18:1n-7), oleic acid (C18:1n-9), y-linolenic acid (C18:3n-6), a-linolenic acid (C18:3n-3), stearidonic acid (C18:4), arachidic acid (C20:0), dihomo-y-linolenic acid (C20:3n-6), arachidonic acid (C20:4n-6, ARA), eicosapentaenoic acid (C20:5n-3, EPA), behenic acid (C22:0), docosatetraenoic acid (C22:4), docosapentaenoic acid n3 (C22:5n-3, DPAn3), and lignoceric acid (C24:0).

6. The method of claim 1, wherein the simple lipid profile comprises less than 0.02% short chain fatty acids.

7. The method of claim 1, wherein the biomass comprises at least 20% protein.

8. The method of claim 1, wherein the biomass comprises at least 20 to 40% protein.

9. The method of claim 1, wherein the biomass comprises at least about 40% protein.

10. The method of claim 1, wherein the lipid composition comprises at least 30% palmitic acid.

11. The method of claim 1, wherein the lipid composition comprises at least 40% palmitic acid.

12. The method of claim 1, wherein the biomass comprises carotenoids.

13. The method of claim 12, wherein at least 95% of the carotenoids comprise B-carotene.

14. The method of claim 1, further comprising incorporating the lipid composition into a foodstuff.

15. The method of claim 14, wherein the foodstuff is pet food, a livestock feed, or an aquaculture feed.

16. The method of claim 1, further comprising incorporating the lipid composition into a nutraceutical or pharmaceutical product.

17. The method of claim 1, further comprising incorporating the lipid composition into a dietary supplement.

18. The method of claim 1, wherein the lipid comprising comprises 35% to 50% DHA.

19. The method of claim 1, wherein the lipid composition comprises 40% to 50% DHA.

20. The method of claim 1, wherein the lipid composition comprises 50% to 60% DHA.

* * * * *

SEQUENCE LISTING

```
<160> NUMBER OF SEQ ID NOS: 19

<210> SEQ ID NO 1
<211> LENGTH: 1770
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (52)..(52)
<223> OTHER INFORMATION: N is A or G
<220> FEATURE:
<221> NAME/KEY: misc_feature
<222> LOCATION: (118)..(118)
<223> OTHER INFORMATION: N is A or T
<220> FEATURE:
<221> NAME/KEY: misc_feature
<222> LOCATION: (127)..(127)
<223> OTHER INFORMATION: N is A or G
<220> FEATURE:
<221> NAME/KEY: misc_feature
<222> LOCATION: (128)..(128)
<223> OTHER INFORMATION: N is C or T
<220> FEATURE:
<221> NAME/KEY: misc_feature
<222> LOCATION: (186)..(186)
<223> OTHER INFORMATION: N is A or G
<220> FEATURE:
<221> NAME/KEY: misc_feature
<222> LOCATION: (255)..(255)
```

```
<223> OTHER INFORMATION: N is A or T
<220> FEATURE:
<221> NAME/KEY: misc_feature
<222> LOCATION: (261)..(261)
<223> OTHER INFORMATION: N is A, G or T
<220> FEATURE:
<221> NAME/KEY: misc_feature
<222> LOCATION: (453)..(453)
<223> OTHER INFORMATION: N is A or G
<220> FEATURE:
<221> NAME/KEY: misc_feature
<222> LOCATION: (454)..(454)
<223> OTHER INFORMATION: N is C or T
<220> FEATURE:
<221> NAME/KEY: misc_feature
<222> LOCATION: (496)..(496)
<223> OTHER INFORMATION: N is A or G
<220> FEATURE:
<221> NAME/KEY: misc_feature
<222> LOCATION: (497)..(497)
<223> OTHER INFORMATION: N is C or T
<220> FEATURE:
<221> NAME/KEY: misc_feature
<222> LOCATION: (557)..(557)
<223> OTHER INFORMATION: N is A or G
<220> FEATURE:
<221> NAME/KEY: misc_feature
<222> LOCATION: (569)..(569)
<223> OTHER INFORMATION: N is A or G
<220> FEATURE:
<221> NAME/KEY: misc_feature
<222> LOCATION: (655)..(655)
<223> OTHER INFORMATION: N is A or T
<220> FEATURE:
<221> NAME/KEY: misc_feature
<222> LOCATION: (684)..(684)
<223> OTHER INFORMATION: N is C or T
<220> FEATURE:
<221> NAME/KEY: misc_feature
<222> LOCATION: (687)..(687)
<223> OTHER INFORMATION: N is A or T
<220> FEATURE:
<221> NAME/KEY: misc_feature
<222> LOCATION: (689)..(689)
<223> OTHER INFORMATION: N is G or T
<220> FEATURE:
<221> NAME/KEY: misc_feature
<222> LOCATION: (690)..(690)
<223> OTHER INFORMATION: N is C or T
<220> FEATURE:
<221> NAME/KEY: misc_feature
<222> LOCATION: (691)..(691)
<223> OTHER INFORMATION: N is C or T
<220> FEATURE:
<221> NAME/KEY: misc_feature
<222> LOCATION: (692)..(692)
<223> OTHER INFORMATION: N is A, G or T
<220> FEATURE:
<221> NAME/KEY: misc_feature
<222> LOCATION: (695)..(695)
<223> OTHER INFORMATION: N is A or T
<220> FEATURE:
<221> NAME/KEY: misc_feature
<222> LOCATION: (697)..(697)
<223> OTHER INFORMATION: N is A or T
<220> FEATURE:
<221> NAME/KEY: misc_feature
<222> LOCATION: (699)..(699)
<223> OTHER INFORMATION: N is A or G
<220> FEATURE:
<221> NAME/KEY: misc_feature
<222> LOCATION: (700)..(700)
<223> OTHER INFORMATION: N is G or T
<220> FEATURE:
<221> NAME/KEY: misc_feature
<222> LOCATION: (701)..(701)
<223> OTHER INFORMATION: N is A or G
<220> FEATURE:
<221> NAME/KEY: misc_feature
```

```
<222> LOCATION: (702)..(702)
<223> OTHER INFORMATION: N is A or T
<220> FEATURE:
<221> NAME/KEY: misc_feature
<222> LOCATION: (705)..(705)
<223> OTHER INFORMATION: N is A or G
<220> FEATURE:
<221> NAME/KEY: misc_feature
<222> LOCATION: (802)..(802)
<223> OTHER INFORMATION: N is C or T
<220> FEATURE:
<221> NAME/KEY: misc_feature
<222> LOCATION: (915)..(915)
<223> OTHER INFORMATION: N is A or C
<220> FEATURE:
<221> NAME/KEY: misc_feature
<222> LOCATION: (925)..(925)
<223> OTHER INFORMATION: N is C or T
<220> FEATURE:
<221> NAME/KEY: misc_feature
<222> LOCATION: (1000)..(1000)
<223> OTHER INFORMATION: N is A or G
<220> FEATURE:
<221> NAME/KEY: misc_feature
<222> LOCATION: (1023)..(1023)
<223> OTHER INFORMATION: N is A or T
<220> FEATURE:
<221> NAME/KEY: misc_feature
<222> LOCATION: (1026)..(1026)
<223> OTHER INFORMATION: N is A, G, or T
<220> FEATURE:
<221> NAME/KEY: misc_feature
<222> LOCATION: (1043)..(1043)
<223> OTHER INFORMATION: N is A or G
<220> FEATURE:
<221> NAME/KEY: misc_feature
<222> LOCATION: (1054)..(1054)
<223> OTHER INFORMATION: N is A or G
<220> FEATURE:
<221> NAME/KEY: misc_feature
<222> LOCATION: (1104)..(1104)
<223> OTHER INFORMATION: N is A or G
<220> FEATURE:
<221> NAME/KEY: misc_feature
<222> LOCATION: (1237)..(1237)
<223> OTHER INFORMATION: N is A or G
<220> FEATURE:
<221> NAME/KEY: misc_feature
<222> LOCATION: (1248)..(1248)
<223> OTHER INFORMATION: N is G or T
<220> FEATURE:
<221> NAME/KEY: misc_feature
<222> LOCATION: (1338)..(1338)
<223> OTHER INFORMATION: N is A or G
<220> FEATURE:
<221> NAME/KEY: misc_feature
<222> LOCATION: (1345)..(1345)
<223> OTHER INFORMATION: N is A or T
<220> FEATURE:
<221> NAME/KEY: misc_feature
<222> LOCATION: (1404)..(1404)
<223> OTHER INFORMATION: N is C or T
<220> FEATURE:
<221> NAME/KEY: misc_feature
<222> LOCATION: (1421)..(1421)
<223> OTHER INFORMATION: N is C or T
<220> FEATURE:
<221> NAME/KEY: misc_feature
<222> LOCATION: (1465)..(1465)
<223> OTHER INFORMATION: N is A or G
<220> FEATURE:
<221> NAME/KEY: misc_feature
<222> LOCATION: (1469)..(1469)
<223> OTHER INFORMATION: N is C or T
<220> FEATURE:
<221> NAME/KEY: misc_feature
<222> LOCATION: (1470)..(1470)
<223> OTHER INFORMATION: N is C or T
<220> FEATURE:
```

```
<221> NAME/KEY: misc_feature
<222> LOCATION: (1472)..(1472)
<223> OTHER INFORMATION: N is A or T
<220> FEATURE:
<221> NAME/KEY: misc_feature
<222> LOCATION: (1475)..(1475)
<223> OTHER INFORMATION: N is A or T
<220> FEATURE:
<221> NAME/KEY: misc_feature
<222> LOCATION: (1476)..(1476)
<223> OTHER INFORMATION: N is A or T
<220> FEATURE:
<221> NAME/KEY: misc_feature
<222> LOCATION: (1529)..(1529)
<223> OTHER INFORMATION: N is C or T
<220> FEATURE:
<221> NAME/KEY: misc_feature
<222> LOCATION: (1546)..(1546)
<223> OTHER INFORMATION: N is C or T
<220> FEATURE:
<221> NAME/KEY: misc_feature
<222> LOCATION: (1563)..(1563)
<223> OTHER INFORMATION: N is A or G
<220> FEATURE:
<221> NAME/KEY: misc_feature
<222> LOCATION: (1630)..(1630)
<223> OTHER INFORMATION: N is C or T
<220> FEATURE:
<221> NAME/KEY: misc_feature
<222> LOCATION: (1678)..(1678)
<223> OTHER INFORMATION: N is A or T
<220> FEATURE:
<221> NAME/KEY: misc_feature
<222> LOCATION: (1681)..(1681)
<223> OTHER INFORMATION: N is C or G
<220> FEATURE:
<221> NAME/KEY: misc_feature
<222> LOCATION: (1692)..(1692)
<223> OTHER INFORMATION: N is A, C or G
<220> FEATURE:
<221> NAME/KEY: misc_feature
<222> LOCATION: (1699)..(1699)
<223> OTHER INFORMATION: N is C or G
<220> FEATURE:
<221> NAME/KEY: misc_feature
<222> LOCATION: (1704)..(1704)
<223> OTHER INFORMATION: N is G or T

<400> SEQUENCE: 1
caacctggtt gatcctgcca gtagtcatat gctcgtctca aagattaagc cntgcatgtg      60
taagtataag cgattgtact gtgagactgc gaacggctca ttatatcagt aataattnct     120
tcggtanntt cttttatatg gataccctgca gtaattctgg aaataataca tgctgtaaga    180
gccctntatg gggctgcact tattagattg aagccgattt tattggtgaa tcatgataat    240
tgagcagatt gactnttttt ngtcgatgaa tcgtttgagt ttctgcccca tcagttgtcg    300
acggtagtgt attggactac ggtgactata acgggtgacg gagagttagg gctcgactcc    360
ggagagggag cctgagagac ggctaccata tccaaggata gcagcaggcg cgtaaattac    420
ccactgtgga ctccacgagg tagtgacgag aannatcgat gcgaagcgtg tatgcgtttt    480
gctatcggaa tgagannaat gtaaaaccct catcgaggat caactggagg gcaagtctgg    540
tgccagcagc cgcggtnatt ccagctccng aagcatatgc taaagttgtt gcagttaaaa    600
agctcgtagt tgaatttctg gcatgggcga ccggtgcttt ccctgaatgg ggatngattg    660
tctgtgttgc cttggccatc tttntcntnn nnttntngnn nnganatctt tcactgtaat    720
caaagcagag tgttccaagc aggtcgtatg accggtatgt ttattatggg atgataagat    780
aggacttggg tgctattttg tnggtttgca cgcctgagta atggttaata ggaacagttg    840
ggggtattcg tatttaggag ctagaggtga aattcttgga tttccgaaag acgaactaga    900
```

```
gcgaaggcat ttacnaagca tgttntcatt aatcaagaac gaaagtctgg ggatcgaaga      960
tgattagata ccatcgtagt ctagaccgta aacgatgccn acttgcgatt gttgggtgct     1020
ttnttntatg ggcctcagca gcngcacatg aganatcaaa gtctttgggt tccgggggga     1080
gtatggtcgc aaggctgaaa cttnaaggaa ttgacggaag ggcaccacca ggagtggagc     1140
ctgcggctta atttgactca acacgggaaa acttaccagg tccagacata ggtaggattg     1200
acagattgag agctctttca tgattctatg ggtggtngtg catggccntt cttagttggt     1260
ggagtgattt gtctggttaa ttccgttaac gaacgagacc tcggcctact aaatagtgcg     1320
tggtatggca acatagtncg ttttnaactt cttagaggga catgtccggt ttacgggcag     1380
gaagttcgag gcaataacag gtcngtgatg cccttagatg ntctgggccg cacgcgcgct     1440
acactgatgg gttcatcggg ttttnattnn anttnntgga attgagtgct tggtcggaag     1500
gcctggctaa tccttggaac gctcatcgng ctggggctag attttngcaa ttattaatct     1560
ccnacgagga attcctagta aacgcaagtc atcagcttgc attgaatacg tccctgccct     1620
ttgtacacan cgcccgtcgc acctaccgat tgaacggtcc gatgaaacca tgggatgntt     1680
ntgtttggat tnattttttng acanaggcag aactcgggtg aatcttattg tttagaggaa     1740
ggtgaagtcg taacaaggtt tccgtagtga                                      1770

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
caacctggtt gatcctgcca gta                                               23

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
tcactacgga aaccttgtta cgac                                              24

<210> SEQ ID NO 4
<211> LENGTH: 17
<212> TYPE: DNA
<213> ORGANISM: Artificial Sequence
<220> FEATURE:
<223> OTHER INFORMATION: Synthetic Construct

<400> SEQUENCE: 4
caggaaacag ctatgac                                                      17

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
taatacgact cactataggg                                                   20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
gtctggtgcc agcagccgcg                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cttaaaggaa ttgacggaag                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
agctttttaa ctgcaacaac                                                    20

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
ggccatgcac caccaccc                                                      18

<210> SEQ ID NO 10
<211> LENGTH: 1761
<212> TYPE: DNA
<213> ORGANISM: Artificial Sequence
<220> FEATURE:
<223> OTHER INFORMATION: Synthetic Construct

<400> SEQUENCE: 10
caacctggtt gatcctgcca gtagtcatat gctcgtctca aagattaagc catgcatgtg        60
taagtataag cgattgtact gtgagactgc gaacggctca ttatatcagt aataatttct       120
tcggtagttt cttttatatg gataccctgca gtaattctgg aaataataca tgctgtaaga     180
gccctgtatg gggctgcact tattagattg aagccgattt tattggtgaa tcatgataat      240
tgagcagatt gacttttag tcgatgaatc gtttgagttt ctgccccatc agttgtcgac        300
ggtagtgtat tggactacgg tgactataac gggtgacgga gagttagggc tcgactccgg      360
agagggagcc tgagagacgg ctaccatatc caaggatagc agcaggcgcg taaattaccc      420
actgtggact ccacgaggta gtgacgagaa atatcgatgc gaagcgtgta tgcgttttgc      480
tatcggaatg agagcaatgt aaaaccctca tcgaggatca actggagggc aagtctggtg     540
ccagcagccg cggtaattcc agctccagaa gcatatgcta agttgttgc agttaaaaag       600 ctcgtagttg aatttctggc atgggcgacc ggtgctttcc ctgaatgggg attgattgtc     660

```
tgtgttgcct tggccatctt tttcttttct ttattgatga gaaatctttc actgtaatca        720
aagcagagtg ttccaagcag gtcgtatgac cggtatgttt attatgggat gataagatag        780
gacttgggtg ctattttgtt ggtttgcacg cctgagtaat ggttaatagg aacagttggg        840
ggtattcgta tttaggagct agaggtgaaa ttcttggatt ccgaaagac gaactagagc         900 gaaggcattt accaagcatg ttttcattaa tcaagaacga aagtctgggg atcgaagatg        960
attagatacc atcgtagtct agaccgtaaa cgatgccaac ttgcgattgt tgggtgcttt       1020
tttatgggcc tcagcagcag cacatgagaa atcaaagtct ttgggttccg ggggagtat        1080 ggtcgcaagg ctgaaactta aaggaattga cggaagggca ccaccaggag tggagcctgc       1140
ggcttaattt gactcaacac gggaaaactt accaggtcca gacataggta ggattgacag       1200
attgagagct ctttcatgat tctatgggtg gtggtgcatg gccgttctta gttggtggag       1260
tgatttgtct ggttaattcc gttaacgaac gagacctcgg cctactaaat agtgcgtggt       1320
atggcaacat agtacgtttt aacttcttag agggacatgt ccggtttacg ggcaggaagt       1380
tcgaggcaat aacaggtctg tgatgccctt agatgctctg ggccgcacgc gcgctacact       1440
gatgggttca tcgggtttta atttcattat tggaattgag tgcttggtcg gaaggcctgg       1500
ctaatccttg gaacgctcat cgtgctgggg ctagattttt gcaattatta atctccaacg       1560
aggaattcct agtaaacgca agtcatcagc ttgcattgaa tacgtccctg ccctttgtac       1620
acaccgcccg tcgcacctac cgattgaacg gtccgatgaa accatgggat gtttgtgttt       1680
ggattcattt ttggacatag gcagaactcg ggtgaatctt attgtttaga ggaaggtgaa       1740
gtcgtaacaa ggtttccgta g                                                 1761
```

<210> SEQ ID NO 11
<211> LENGTH: 1764
<212> TYPE: DNA
<213> ORGANISM: Artificial Sequence
<220> FEATURE:
<223> OTHER INFORMATION: Synthetic Construct

<400> SEQUENCE: 11

```
aacctggttg atcctgccag tagtcatatg ctcgtctcaa agattaagcc atgcatgtgt         60
aagtataagc gattgtactg tgagactgcg aacggctcat tatatcagta ataatttctt        120
cggtagtttc tttatatgg atacctgcag taattctgga ataatacat gctgtaagag          180 ccctgtatgg ggctgcactt attagattga agccgatttt attggtgaat catgataatt        240
gagcagattg acttttagt cgatgaatcg tttgagtttc tgccccatca gttgtcgacg         300
gtagtgtatt ggactacggt gactataacg ggtgacggag agttagggct cgactccgga        360
gagggagcct gagagacggc taccatatcc aaggatagca gcaggcgcgt aaattaccca       420
ctgtggactc cacgaggtag tgacgagaaa tatcgatgcg aagcgtgtat gcgttttgct       480
atcggaatga gagcaatgta aaaccctcat cgaggatcaa ctggagggca agtctggtgc       540
cagcagccgc ggtaattcca gctccagaag catatgctaa agttgttgca gttaaaaagc      600
tcgtagttga atttctggca tgggcgaccg gtgctttccc tgaatgggga tagattgtct       660
gtgttgcctt ggccatcttt ttctttcttt tttaggggag aaatctttca ctgtaatcaa       720
agcagagtgt tccaagcagg tcgtatgacc ggtatgttta ttatgggatg ataagatagg       780
acttgggtgc tattttgtcg gtttgcacgc ctgagtaatg gttaatagga acagttgggg       840
gtattcgtat ttaggagcta gaggtgaaat tcttggattt ccgaaagacg aactagagcg       900
```

| | |
|---|---:|
| aaggcattta ccaagcatgt tttcattaat caagaacgaa agtctgggga tcgaagatga | 960 |
| ttagatacca tcgtagtcta daccgtaaac gatgccgact tgcgattgtt gggtgctttt | 1020 |
| ttatgggcct cagcagcagc acatgagaaa tcaaagtctt tgggttccgg ggggagtatg | 1080 |
| gtcgcaaggc tgaaacttaa aggaattgac ggaagggcac caccaggagt ggagcctgcg | 1140 |
| gcttaatttg actcaacacg ggaaaactta ccaggtccag acataggtag gattgacaga | 1200 |
| ttgagagctc tttcatgatt ctatgggtgg tagtgcatgg ccgttcttag ttggtggagt | 1260 |
| gatttgtctg gttaattccg ttaacgaacg agacctcggc ctactaaata gtgcgtggta | 1320 |
| tggcaacata gtacgttttt acttcttaga gggacatgtc cggtttacgg gcaggaagtt | 1380 |
| cgaggcaata acaggtctgt gatgccctta gatgttctgg gccgcacgcg cgctacactg | 1440 |
| atgggttcat cgggttttga ttctatttta tggaattgag tgcttggtcg gaaggcctgg | 1500 |
| ctaatccttg gaacgctcat cgtgctgggg ctagattttt gcaattatta atctccaacg | 1560 |
| aggaattcct agtaaacgca agtcatcagc ttgcattgaa tacgtccctg cccttttgtac | 1620 |
| acaccgcccg tcgcacctac cgattgaacg gtccgatgaa accatgggat gattctgttt | 1680 |
| ggattaattt ttggacagag gcagaactcg ggtgaatctt attgtttaga ggaaggtgaa | 1740 |
| gtcgtaacaa ggtttccgta gtga | 1764 |

<210> SEQ ID NO 12
<211> LENGTH: 1765
<212> TYPE: DNA
<213> ORGANISM: Artificial Sequence
<220> FEATURE:
<223> OTHER INFORMATION: Synthetic Construct

<400> SEQUENCE: 12

| | |
|---|---:|
| caacctggtt gatcctgcca gtagtcatat gctcgtctca aagattaagc cgtgcatgtg | 60 |
| taagtataag cgattgtact gtgagactgc gaacggctca ttatatcagt aataatttct | 120 |
| tcggtagctt cttttatatg gatacctgca gtaattctgg aaataataca tgctgtaaga | 180 |
| gccctgtatg gggctgcact tattagattg aagccgattt tattggtgaa tcatgataat | 240 |
| tgagcagatt gactatttt ggtcgatgaa tcgtttgagt ttctgcccca tcagttgtcg | 300 |
| acggtagtgt attggactac ggtgactata acgggtgacg gagagttagg gctcgactcc | 360 |
| ggagagggag cctgagagac ggctaccata tccaaggata gcagcaggcg cgtaaattac | 420 |
| ccactgtgga ctccacgagg tagtgacgag aaatatcgat gcgaagcgtg tatgcgtttt | 480 |
| gctatcggaa tgagagcaat gtaaaaccct catcgaggat caactggagg gcaagtctgg | 540 |
| tgccagcagc cgcggtaatt ccagctccag aagcatatgc taaagttgtt gcagttaaaa | 600 |
| agctcgtagt tgaatttctg gcatgggcga ccggtgcttt ccctgaatgg ggattgattg | 660 |
| tctgtgttgc cttggccatc tttctcatgc tattttggta tgagatcttt cactgtaatc | 720 |
| aaagcagagt gttccaagca ggtcgtatga ccggtatgtt tattatggga tgataagata | 780 |
| ggacttgggt gctattttgt tggtttgcac gcctgagtaa tggttaatag gaacagttgg | 840 |
| gggtattcgt atttaggagc tagaggtgaa attcttggat ttccgaaaga cgaactagag | 900 |
| cgaaggcatt tacaaagcat gttttcatta atcaagaacg aaagtctggg gatcgaagat | 960 |
| gattagatac catcgtagtc tagaccgtaa acgatgccga cttgcgattg ttgggtgctt | 1020 |
| ttttatgggg cctcagcagc ggcacatgag aaatcaaagt cttgggttc ggggggagt | 1080 |
| atggtcgcaa ggctgaaact tgaaggaatt gacggaaggg cacaccagga gtggagcctg | 1140 |
| cggcttaatt tgactcaaca cgggaaaact taccaggtcc agacataggt aggattgaca | 1200 |

```
gattgagagc tctttcatga ttctatgggt ggtggtgcat ggccgttctt agttggtgga   1260
gtgatttgtc tggttaattc cgttaacgaa cgagacctcg gcctactaaa tagtgcgtgg   1320
tatggcaaca tagtacgttt taacttctta gagggacatg tccggtttac gggcaggaag   1380
ttcgaggcaa taacaggtct gtgatgccct tagatgttct gggccgcacg cgcgctacac   1440
tgatgggttc atcgggtttt aattctattt ttggaattga gtgcttggtc ggaaggcctg   1500
gctaatcctt ggaacgctca tcgtgctggg gctagatttt tgcaattatt aatctccaac   1560
gaggaattcc tagtaaacgc aagtcatcag cttgcattga atacgtccct gcccttgta    1620 cacatcgccc gtcgcaccta ccgattgaac ggtccgatga aaccatggga tgtttgtgtt   1680
tggattaatt tttggacaga ggcagaactc gggtgaatct tattgtttag aggaaggtga   1740
agtcgtaaca aggtttccgt agtga                                         1765
```

<210> SEQ ID NO 13
<211> LENGTH: 1767
<212> TYPE: DNA
<213> ORGANISM: Artificial Sequence
<220> FEATURE:
<223> OTHER INFORMATION: Synthetic Construct

<400> SEQUENCE: 13

```
caacctggtt gatcctgcca gtagtcatat gctcgtctca aagattaagc catgcatgtg     60
taagtataag cgattgtact gtgagactgc gaacggctca ttatatcagt ataatttct    120 tcggtagttt cttttatatg gatacctgca gtaattctgg aaataataca tgctgtaaga   180
gccctgtatg gggctgcact tattagattg aagccgattt tattggtgaa tcatgataat   240
tgagcagatt gactattttt gtcgatgaat cgtttgagtt tctgccccat cagttgtcga   300
cggtagtgta ttggactacg gtgactataa cgggtgacgg agagttaggg ctcgactccg   360
gagagggagc ctgagagacg gctaccatat ccaaggatag cagcaggcgc gtaaattacc   420
cactgtggac tccacgaggt agtgacgaga agtatcgatg cgaagcgtgt atgcgttttg   480
ctatcggaat gagagcaatg taaaaccctc atcgaggatc aactggaggg caagtctggt   540
gccagcagcc gcggtaattc cagctccgga agcatatgct aaagttgttg cagttaaaaa    600
gctcgtagtt gaatttctgg catgggcgac cggtgctttc cctgaatggg gatagattgt   660
ctgtgttgcc ttggccatct ttttcttttc tttattgatg agaaatcttt cactgtaatc   720
aaagcagagt gttccaagca ggtcgtatga ccggtatgtt tattatggga tgataagata   780
ggacttgggt gctattttgt tggtttgcac gcctgagtaa tggttaatag gaacagttgg   840
gggtattcgt atttaggagc tagaggtgaa attcttggat ttccgaaaga cgaactagag   900
cgaaggcatt taccaagcat gttctcatta atcaagaacg aaagtctggg gatcgaagat   960
gattagatac catcgtagtc tagaccgtaa acgatgccga cttgcgattg ttgggtgctt   1020
tattatatgg gcctcagcag cagcacatga gaaatcaaag tctttgggtt ccgggggag    1080 tatggtcgca aggctgaaac ttaaaggaat tgacggaagg gcaccaccag gagtggagcc   1140
tgcggcttaa tttgactcaa cacgggaaaa cttaccaggt ccagacatag gtaggattga   1200
cagattgaga gctctttcat gattctatgg gtggtggtgc atggccttc ttagttggtg    1260 gagtgatttg tctggttaat tccgttaacg aacgagacct cggcctacta aatagtgcgt   1320
ggtatggcaa catagtgcgt ttttacttct tagagggaca tgtccggttt acgggcagga   1380
agttcgaggc aataacaggt ctgtgatgcc cttagatgtt ctgggccgca cgcgcgctac   1440
```

| actgatgggt tcatcgggtt ttaatttcat ttttggaatt gagtgcttgg tcggaaggcc | 1500 |
| tggctaatcc ttggaacgct catcgtgctg gggctagatt ttcgcaatta ttaatctcca | 1560 |
| acgaggaatt cctagtaaac gcaagtcatc agcttgcatt gaatacgtcc ctgcccttttg | 1620 |
| tacacaccgc ccgtcgcacc taccgattga acggtccgat gaaaccatgg gatgtttctg | 1680 |
| tttggattga ttttcgaca gaggcagaac tcgggtgaat cttattgttt agaggaaggt | 1740 |
| gaagtcgtaa caaggtttcc gtagtga | 1767 |

```
<210> SEQ ID NO 14
<211> LENGTH: 1761
<212> TYPE: DNA
<213> ORGANISM: Artifcial Sequence
<220> FEATURE:
<223> OTHER INFORMATION: Synthetic Construct

<400> SEQUENCE: 14
```

| caacctggtt gatcctgcca gtagtcatat gctcgtctca aagattaagc catgcatgtg | 60 |
| taagtataag cgattgtact gtgagactgc gaacggctca ttatatcagt aataatttct | 120 |
| tcggtagttt ctttttatatg gatacctgca gtaattctgg aaataataca tgctgtaaga | 180 |
| gccctgtatg gggctgcact tattagattg aagccgattt tattggtgaa tcatgataat | 240 |
| tgagcagatt gactttttag tcgatgaatc gtttgagttt ctgccccatc agttgtcgac | 300 |
| ggtagtgtat tggactacgg tgactataac gggtgacgga gagttagggc tcgactccgg | 360 |
| agagggagcc tgagagacgg ctaccatatc caaggatagc agcaggcgcg taaattaccc | 420 |
| actgtggact ccacgaggta gtgacgagaa atatcgatgc gaagcgtgta tgcgttttgc | 480 |
| tatcggaatg agagcaatgt aaaaccctca tcgaggatca actggagggc aagtctggtg | 540 |
| ccagcagccg cggtaattcc agctccagaa gcatatgcta agttgttgc agttaaaaag | 600 |
| ctcgtagttg aatttctggc atgggcgacc ggtgctttcc ctgaatgggg attgattgtc | 660 |
| tgtgttgcct tggccatctt tttcttttct ttattgatga gaaatctttc actgtaatca | 720 |
| aagcagagtg ttccaagcag gtcgtatgac cggtatgttt attatgggat gataagatag | 780 |
| gacttgggtg ctatttttgtt ggtttgcacg cctgagtaat ggttaatagg aacagttggg | 840 |
| ggtattcgta tttaggagct agaggtgaaa ttcttggatt tccgaaagac gaactagagc | 900 |
| gaaggcattt accaagcatg ttttcattaa tcaagaacga aagtctgggg atcgaagatg | 960 |
| attagatacc atcgtagtct agaccgtaaa cgatgccaac ttgcgattgt tgggtgcttt | 1020 |
| tttatgggcc tcagcagcag cacatgagaa atcaaagtct ttgggttccg gggggagtat | 1080 |
| ggtcgcaagg ctgaaactta aaggaattga cggaagggca ccaccaggag tggagcctgc | 1140 |
| ggcttaatttt gactcaacac gggaaaactt accaggtcca gacataggta ggattgacag | 1200 |
| attgagagct ctttcatgat tctatgggtg gtggtgcatg gccgttctta gttggtggag | 1260 |
| tgatttgtct ggttaattcc gttaacgaac gagacctcgg cctactaaat agtgcgtggt | 1320 |
| atggcaacat agtacgtttt aacttcttag agggacatgt ccggtttacg ggcaggaagt | 1380 |
| tcgaggcaat aacaggtctg tgatgcccct agatgctctg gccgcacgc gcgctacact | 1440 |
| gatgggttca tcgggtttta atttcattat tggaattgag tgcttggtcg gaaggcctgg | 1500 |
| ctaatccttg gaacgctcat cgtgctgggg ctagattttt gcaattatta atctccaacg | 1560 |
| aggaattcct agtaaacgca agtcatcagc ttgcattgaa tacgtccctg cccttttgtac | 1620 |
| acaccgcccg tcgcacctac cgattgaacg gtccgatgaa accatgggat gtttgtgttt | 1680 |
| ggattcattt ttgacatag gcagaactcg ggtgaatctt attgtttaga ggaaggtgaa | 1740 |

```
gtcgtaacaa ggtttccgta g                                                  1761
```

<210> SEQ ID NO 15
<211> LENGTH: 1767
<212> TYPE: DNA
<213> ORGANISM: Artificial Sequence
<220> FEATURE:
<223> OTHER INFORMATION: Synthetic Construct

<400> SEQUENCE: 15

```
caacctggtt gatccgccag tagtcatatg ctcgtctcaa agattaagcc atgcatgtgt          60
aagtataagc gattgtactg tgagactgcg aacggctcat tatatcagta ataatttctt         120
cggtaatttc ttttatatgg atacctgcag taattctgga ataatacat gctgtaagag          180
ccctgtatgg ggctgcactt attagattga agccgatttt attggtgaat catgataatt         240
gagcagattg acttttttgg tcgatgaatc gtttgagttt ctgccccatc agttgtcgac         300
ggtagtgtat tggactacgg tgactataac gggtgacgga gagttaggc tcgactccgg          360
agagggagcc tgagagacgg ctaccatatc caaggatagc agcaggcgcg taaattaccc         420
actgtggact ccacgaggta gtgacgagaa acatcgatgc gaagcgtgta tgcgttttgc         480
tatcggaatg agaacaatgt aaaaccctca tcgaggatca actggagggc aagtctggtg         540
ccagcagccg cggtaattcc agctccagaa gcatatgcta agttgttgc agttaaaaag          600
ctcgtagttg aatttctggc atgggcgacc ggtgctttcc ctgaatgggg attgattgtc         660
tgtgttgcct tggccatctt tctcatgctg ttattggtat gagatctttc actgtaatca         720
aagcagagtg ttccaagcag gtcgtatgac cggtatgttt attatgggat gataagatag         780
gacttgggtg ctattttgtt ggtttgcacg cctgagtaat ggttaatagg aacagttggg         840
ggtattcgta tttaggagct agaggtgaaa ttcttggatt ccgaaagac gaactagagc          900
gaaggcattt accaagcatg ttttcattaa tcaagaacga aagtctgggg atcgaagatg         960
attagatacc atcgtagtct agaccgtaaa cgatgccgac ttgcgattgt tgggtgcttt        1020
tttgtatggg cctcagcagc agcacatgag aaatcaaagt ctttgggttc cggggggagt        1080
atggtcgcaa ggctgaaact taaaggaatt gacgaaggg caccaccagg agtggagcct         1140
gcggcttaat ttgactcaac acgggaaaac ttaccaggtc cagacatagg taggattgac        1200
agattgagag ctcttttcatg attctatggg tggtggtgca tggccgttct tagttggtgg      1260
agtgatttgt ctggttaatt ccgttaacga acgagacctc ggcctactaa atagtgcgtg        1320
gtatggcaac atagtacgtt ttaacttctt agagggacat gtccggttta cgggcaggaa      1380
gttcgaggca ataacaggtc tgtgatgccc ttagatgttc tgggccgcac gcgcgctaca        1440
ctgatgggtt catcgggttt taattctaat ttttggaatt gagtgcttgg tcggaaggcc      1500
tggctaatcc ttgaacgct catcgcgctg gggctagatt tttgcaatta ttaatctcca       1560
acgaggaatt cctagtaaac gcaagtcatc agcttgcatt gaatacgtcc ctgcccttg        1620
tacacaccgc ccgtcgcacc taccgattga acggtccgat gaaaccatgg gatgtttctg      1680
tttggattca tttttggaca gaggcagaac tcgggtgaat cttattgttt agaggaaggt      1740
gaagtcgtaa caaggtttcc gtagtga                                           1767
```

<210> SEQ ID NO 16
<211> LENGTH: 1765
<212> TYPE: DNA
<213> ORGANISM: Artificial Sequence
<220> FEATURE:

<223> OTHER INFORMATION: Synthetic Construct

<400> SEQUENCE: 16

```
caacctggtt gatcctgcca gtagtcatat gctcgtctca aagattaagc catgcatgtg    60
taagtataag cgattgtact gtgagactgc aacggctca ttatatcagt aataatttct   120
tcggtagttt cttttatatg gataccctgca gtaattctgg aaataataca tgctgtaaga   180
gccctatatg gggctgcact tattagattg aagccgattt tattggtgaa tcatgataat   240
tgagcagatt gacttttag tcgatgaatc gtttgagttt ctgccccatc agttgtcgac   300
ggtagtgtat tggactacgg tgactataac gggtgacgga gagttagggc tcgactccgg   360
agagggagcc tgagagacgg ctaccatatc caaggatagc agcaggcgcg taaattaccc   420
actgtggact ccacgaggta gtgacgagaa atatcgatgc gaagcgtgta tgcgttttgc   480
tatcggaatg agagcaatgt aaaaccctca tcgaggatca actggagggc aagtctggtg   540
ccagcagccg cggtaattcc agctccagaa gcatatgcta agttgttgc agttaaaaag   600
ctcgtagttg aatttctggc atgggcgacc ggtgctttcc ctgaatgggg attgattgtc   660
tgtgttgcct tggccatctt tttctttct ttaggga gaaatctttc actgtaatca   720
aagcagagtg ttccaagcag gtcgtatgac cggtatgttt attatgggat gataagatag   780
gacttgggtg ctattttgtt ggtttgcacg cctgagtaat ggttaatagg aacagttggg   840
ggtattcgta tttaggagct agaggtgaaa ttcttggatt ccgaaagac gaactagagc   900
gaaggcattt accaagcatg ttttcattaa tcaagaacga agtctgggg atcgaagatg   960
attagatacc atcgtagtct agaccgtaaa cgatgccgac ttgcgattgt tgggtgcttt  1020
tttatgggcc tcagcagcag cacatgagag atcaaagtct ttgggttccg gggggagtat  1080
ggtcgcaagg ctgaaactta aaggaattga cggaagggca ccaccaggag tggagcctgc  1140
ggcttaattt gactcaacac gggaaaactt accaggtcca gacataggta ggattgacag  1200
attgagagct ctttcatgat tctatgggtg gtgtgcatg gccgttctta gttggtggag  1260
tgatttgtct ggttaattcc gttaacgaac gagacctcgg cctactaaat agtgcgtggt  1320
atggcaacat agtacgtttt tacttcttag agggacatgt ccggtttacg ggcaggaagt  1380
tcgaggcaat aacaggtccg tgatgccctt agatgttctg ggccgcacgc gcgctacact  1440
gatgggttca tcgggttttg attctatttt atggaattga gtgcttggtc ggaaggcctg  1500
gctaatcctt ggaacgctca tcgtgctggg ctagatttt tgcaattatt aatctccaac  1560
gaggaattcc tagtaaacgc aagtcatcag cttgcattga atacgtccct gcccttgta  1620
cacaccgccc gtcgcaccta ccgattgaac ggtccgatga aaccatggga tgtttctgtt  1680
tggattaatt tttggacaga ggcagaactc gggtgaatct tattgtttag aggaaggtga  1740
agtcgtaaca aggtttccgt agtga                                        1765
```

<210> SEQ ID NO 17
<211> LENGTH: 1765
<212> TYPE: DNA
<213> ORGANISM: Artificial Sequence
<220> FEATURE:
<223> OTHER INFORMATION: Synthetic Construct

<400> SEQUENCE: 17

```
caacctggtt gatcctgcca gtagtcatat gctcgtctca aagattaagc catgcatgtg    60
taagtataag cgattgtact gtgagactgc aacggctca ttatatcagt aataatttct   120
tcggtagttt cttttatatg gataccctgca gtaattctgg aaataataca tgctgtaaga   180
```

```
gccctatatg gggctgcact tattagattg aagccgattt tattggtgaa tcatgataat      240
tgagcagatt gacttttag tcgatgaatc gtttgagttt ctgccccatc agttgtcgac       300
ggtagtgtat tggactacgg tgactataac gggtgacgga gagttagggc tcgactccgg      360
agagggagcc tgagagacgg ctaccatatc caaggatagc agcaggcgcg taaattaccc      420
actgtggact ccacgaggta gtgacgagaa atatcgatgc gaagcgtgta tgcgttttgc      480
tatcggaatg agagcaatgt aaaaccctca tcgaggatca actggagggc aagtctggtg      540
ccagcagccg cggtaattcc agctccagaa gcatatgcta agttgttgc agttaaaaag       600 ctcgtagttg aatttctggc atgggcgacc ggtgctttcc ctgaatgggg attgattgtc      660
tgtgttgcct tggccatctt tttctttct ttaggggga gaaatctttc actgtaatca       720
aagcagagtg ttccaagcag gtcgtatgac cggtatgttt attatgggat gataagatag     780
gacttgggtg ctatttgtt ggtttgcacg cctgagtaat ggttaatagg aacagttggg      840
ggtattcgta tttaggagct agaggtgaaa ttcttggatt ccgaaagac gaactagagc      900 gaaggcattt accaagcatg ttttcattaa tcaagaacga agtctgggg atcgaagatg       960 attagatacc atcgtagtct agaccgtaaa cgatgccgac ttgcgattgt tgggtgcttt     1020
tttatgggcc tcagcagcag cacatgagag atcaaagtct ttgggttccg ggggagtat      1080 ggtcgcaagg ctgaaactta aaggaattga cggaagggca ccaccaggag tggagcctgc     1140
ggcttaattt gactcaacac gggaaaactt accaggtcca gacataggta ggattgacag     1200
attgagagct ctttcatgat tctatgggtg gtggtgcatg gccgttctta gttggtggag     1260
tgatttgtct ggttaattcc gttaacgaac gagacctcgg cctactaaat agtgcgtggt     1320
atggcaacat agtacgtttt tacttcttag agggacatgt ccggtttacg ggcaggaagt     1380
tcgaggcaat aacaggtccg tgatgccctt agatgttctg ggccgcacgc gcgctacact     1440
gatgggttca tcgggttttg attctatttt atggaattga gtgcttggtc ggaaggcctg     1500
gctaatcctt ggaacgctca tcgtgctggg gctagatttt tgcaattatt aatctccaac     1560
gaggaattcc tagtaaacgc aagtcatcag cttgcattga atacgtccct gccctttgta     1620
cacaccgccc gtcgcaccta ccgattgaac ggtccgatga accatggga tgtttctgtt      1680 tggattaatt tttggacaga ggcagaactc gggtgaatct tattgtttag aggaaggtga     1740
agtcgtaaca aggtttccgt agtga                                           1765
```

<210> SEQ ID NO 18
<211> LENGTH: 1767
<212> TYPE: DNA
<213> ORGANISM: Artificial Sequence
<220> FEATURE:
<223> OTHER INFORMATION: Synthetic Construct

<400> SEQUENCE: 18

```
caacctggtt gatcctgcca gtagtcatat gctcgtctca agattaagc catgcatgtg        60 taagtataag cgattgtact gtgagactgc gaacggctca ttatatcagt ataatttct       120 tcggtagttt cttttatatg gatacctgca gtaattctgg aaataataca tgctgtaaga     180
gccctgtatg gggctgcact tattagattg aagccgattt tattggtgaa tcatgataat     240
tgagcagatt gactattttg gtcgatgaat cgtttgagtt tctgccccat cagttgtcga     300
cggtagtgta ttggactacg gtgactataa cgggtgacgg agagttaggg ctcgactccg     360
gagagggagc ctgagagacg gctaccatat ccaaggatag cagcaggcgc gtaaattacc     420
```

```
cactgtggac tccacgaggt agtgacgaga aatatcgatg cgaagcgtgt atgcgttttg      480
ctatcggaat gagagtaatg taaaaccctc atcgaggatc aactggaggg caagtctggt      540
gccagcagcc gcggtaattc cagctccaga agcatatgct aaagttgttg cagttaaaaa      600
gctcgtagtt gaattctgg catgggcgac cggtgctttc cctgaatggg gattgattgt       660
ctgtgttgcc ttggccatct ttttcttttc tttattgggg agaaatcttt cactgtaatc      720
aaagcagagt gttccaagca ggtcgtatga ccggtatgtt tattatggga tgataagata      780
ggacttgggt gctattttgt tggtttgcac gcctgagtaa tggttaatag aacagttgg       840 gggtattcgt atttaggagc tagaggtgaa attcttggat ttccgaaaga cgaactagag      900
cgaaggcatt taccaagcat gttttcatta atcaagaacg aaagtctggg gatcgaagat     960
gattagatac catcgtagtc tagaccgtaa acgatgccga cttgcgattg ttgggtgctt      1020
ttttatgggc ctcagcagca gcacatgaga aatcaaagtc tttgggttcc ggggggagta      1080
tggtcgcaag gctgaaactt aaaggaattg acgaagggc accaccagga gtggagcctg       1140
cggcttaatt tgactcaaca cgggaaaact taccaggtcc agacataggt aggattgaca      1200
gattgagagc tctttcatga ttctatgggt ggtggtgcat ggccgttctt agttggtgga      1260
gtgatttgtc tggttaattc cgttaacgaa cgagacctcg gcctactaaa tagtgcgtgg      1320
tatggcaaca tagtgcgttt ttaacttctt agagggacat gtccggttta cgggcaggaa      1380
gttcgaggca ataacaggtc tgtgatgccc ttagatgttc tgggccgcac gcgcgctaca      1440
ctgatgggtt catcgggttt taatttcatt taatggaatt gagtgcttgg tcggaaggcc      1500
tggctaatcc ttgaacgct catcgtgctg ggctagattt tttgcaatta ttaatctcca      1560
acgaggaatt cctagtaaac gcaagtcatc agcttgcatt gaatacgtcc ctgcccttttg     1620 tacacaccgc ccgtcgcacc taccgattga acggtccgat gaaaccatgg gatgtttgtg      1680
tttggattaa tttttggaca taggcagaac tcgggtgaat cttattgttt agaggaaggt      1740
gaagtcgtaa caaggtttcc gtagtga                                           1767
```

<210> SEQ ID NO 19
<211> LENGTH: 1769
<212> TYPE: DNA
<213> ORGANISM: Artificial Sequence
<220> FEATURE:
<223> OTHER INFORMATION: Synthetic Construct

<400> SEQUENCE: 19

```
caacctggtt gatcctgcca gtagtcatat gctcgtctca aagattaagc catgcatgtg       60
taagtataag cgattgtact gtgagactgc gaacggctca ttatatcagt ataaattact      120
tcggtagttt cttttatatg gatacctgca gtaattctgg aaataataca tgctgtaaga     180
gccctgtatg gggctgcact tattagattg aagccgattt tattggtgaa tcatgataat      240
tgagcagatt gactattttt ggtcgatgaa tcgtttgagt ttctgcccca tcagttgtcg      300
acggtagtgt attggactac ggtgactata acggtgacg agagttagg gctcgactcc        360 ggagagggag cctgagagac ggctaccata tccaaggata gcagcaggcg cgtaaattac     420
ccactgtgga ctccacgagg tagtgacgag aaatatcgat gcgaagcgtg tatgcgtttt     480
gctatcggaa tgagagcaat gtaaaaccct catcgaggat caactggagg gcaagtctgg    540
tgccagcagc cgcggtgatt ccagctccag aagcatatgc taaagttgtt gcagttaaaa    600
agctcgtagt tgaattctg catgggcgac ccggtgcttt cctgaatgg ggattgattg       660 tctgtgttgc cttggccatc ttttcttttc ttattggg gagaaatctt tcactgtaat       720
```

-continued

```
caaagcagag tgttccaagc aggtcgtatg accggtatgt ttattatggg atgataagat    780
aggacttggg tgctattttg ttggtttgca cgcctgagta atggttaata ggaacagttg    840
ggggtattcg tatttaggag ctagaggtga aattcttgga tttccgaaag acgaactaga    900
gcgaaggcat ttaccaagca tgttttcatt aatcaagaac gaaagtctgg ggatcgaaga    960
tgattagata ccatcgtagt ctagaccgta aacgatgccg acttgcgatt gttgggtgct   1020
ttttttatg ggcctcagca gcagcacatg agaaatcaaa gtctttgggt tccggggga    1080
gtatggtcgc aaggctgaaa cttaaaggaa ttgacggaag ggcaccacca ggagtggagc   1140
ctgcggctta atttgactca acacgggaaa acttaccagg tccagacata ggtaggattg   1200
acagattgag agctctttca tgattctatg ggtggtggtg catggccgtt cttagttggt   1260
ggagtgattt gtctggttaa ttccgttaac gaacgagacc tcggcctact aaatagtgcg   1320
tggtatggca acatagtacg tttttacttc ttagagggac atgtccggtt tacgggcagg   1380
aagttcgagg caataacagg tctgtgatgc ccttagatgt tctgggccgc acgcgcgcta   1440
cactgatggg ttcatcgggt tttaatttca attttggaa ttgagtgctt ggtcggaagg   1500
cctggctaat ccttggaacg ctcatcgtgc tggggctaga tttttgcaat tattaatctc   1560
cgacgaggaa ttcctagtaa acgcaagtca tcagcttgca ttgaatacgt ccctgccctt   1620
tgtacacacc gcccgtcgca cctaccgatt gaacggtccg atgaaaccat gggatgtttc   1680
tgtttggatt cattttgga cagaggcaga actcgggtga atcttattgt ttagaggaag   1740
gtgaagtcgt aacaaggttt ccgtagtga                                     1769
```